United States Patent
Peltola et al.

(10) Patent No.: US 11,278,737 B2
(45) Date of Patent: Mar. 22, 2022

(54) SYSTEMS AND METHODS FOR AUTOMATIC TREATMENT PLANNING AND OPTIMIZATION

(71) Applicant: VARIAN MEDICAL SYSTEMS INTERNATIONAL AG, Steinhausen (CH)

(72) Inventors: Jarkko Peltola, Tuusula (FI); Pauli Suhonen, Helsinki (FI); Christopher Boylan, Helsinki (FI); Stephen Thompson, Palo Alto, CA (US); Esa Kuusela, Helsinki (FI)

(73) Assignee: VARIAN MEDICAL SYSTEMS INTERNATIONAL AG, Steinhausen (CH)

(*) Notice: Subject to any disclaimer, the term of this patent is extended or adjusted under 35 U.S.C. 154(b) by 183 days.

(21) Appl. No.: 16/564,924

(22) Filed: Sep. 9, 2019

(65) Prior Publication Data
US 2021/0069527 A1    Mar. 11, 2021

(51) Int. Cl.
*A61N 5/10* (2006.01)
*G06N 7/00* (2006.01)
*G06F 17/10* (2006.01)

(52) U.S. Cl.
CPC ......... *A61N 5/1031* (2013.01); *A61N 5/1075* (2013.01); *G06F 17/10* (2013.01); *A61N 2005/1074* (2013.01)

(58) Field of Classification Search
CPC .......... A61N 5/1031; A61N 2005/1034; A61N 2005/1041; A61N 2005/1074; A61N 5/1075; A61N 5/1077; A61N 5/1038; G06N 20/00; G06N 7/005

See application file for complete search history.

(56) References Cited

U.S. PATENT DOCUMENTS

| | | | |
|---|---|---|---|
| 7,831,289 B2 | 11/2010 | Riker et al. | |
| 9,844,684 B2 | 12/2017 | Luan et al. | |
| 10,022,560 B2 | 7/2018 | Kumar et al. | |
| 10,143,859 B2 | 12/2018 | Ollila et al. | |
| 10,188,873 B2 | 1/2019 | Kuusela et al. | |
| 2020/0206533 A1* | 7/2020 | Laaksonen | A61N 5/1031 |

FOREIGN PATENT DOCUMENTS

| | | |
|---|---|---|
| EP | 3 229 905 A1 | 10/2017 |
| WO | WO 2019/025460 A1 | 2/2019 |

OTHER PUBLICATIONS

International Search Report and Written Opinion dated Feb. 8, 2021, in PCT Application No. PCT/EP2020/075105.
Kessler et al, "Costlets: A Generalized Approach to Cost Functions for Automated Optimization of IMRT Treatment Plans", Optimization and Engineering; International Multidisciplinary Journal to Promote Optimizational Theory & Applications in Engin, Kluwer Academic Publishers, BO, vol. 6, No. 4, Dec. 1, 2005, pp. 421-448.
(Continued)

*Primary Examiner* — Don K Wong
(74) *Attorney, Agent, or Firm* — SGPatents PLLC

(57) ABSTRACT

Systems and methods for the automatic generation and optimization of radiation therapy treatment plans, and systems and methods for the automatic generation and optimization of an adapted plan in an adaptive radiation therapy workflow.

13 Claims, 16 Drawing Sheets

(56) References Cited

OTHER PUBLICATIONS

Zarepisheh et al., "A DVH-guided IMRT optimization algorithm for automatic treatment planning and adaptive radiotherapy replanning", Medical Physics, vol. 41, No. 6, Jun. 1, 2014, pp. 061711.
Invitation to Pay Additional Fees and Partial International Search dated Dec. 18, 2020, in PCT Application No. PCT/EP2020/075105.
Krayenbuehl et al., "Evaluation of an automated knowledge based treatment planning system for head and neck," BioMed Central, Radiation Oncology, 2015.
Smith et al., "Personalized treatment planning with a model of radiation therapy outcomes for use in multiobjective optimization of IMRT plans for prostate cancer," BioMed Central, Radiation Oncology, 2016.
Barbiere et al., "A parameter optimization algorithm for intensity-modulated radiotherapy prostate treatment planning," Journal Of Applied Clinical Medical Physics, vol. 3, No. 3, Summer 2002.
Dumane et al., "Training and evaluation of a knowledge-based model for automated treatment planning of multiple brain metastases," Journal of Cancer Metastasis and Treatment, 2019.
Oliver et al., "Analysis of RapidArc optimization strategies using objective function values and dose-volume histograms," Journal Of Applied Clinical Medical Physics, vol. 11, No. 1, Winter 2010.

\* cited by examiner

FIG. 18
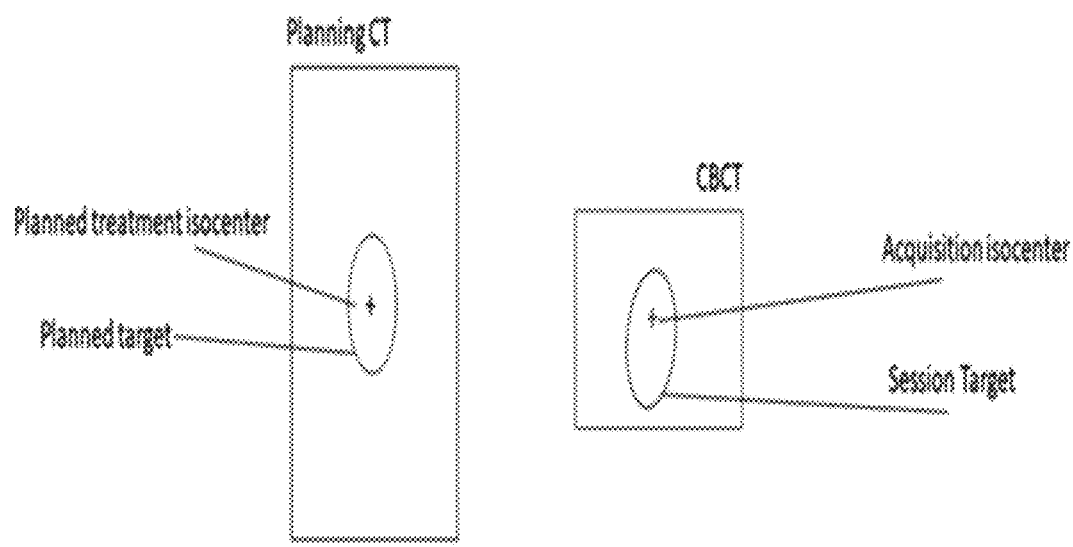
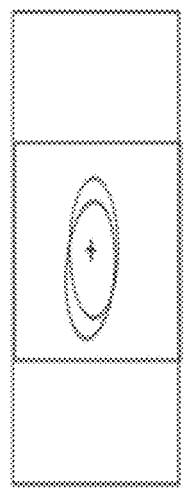
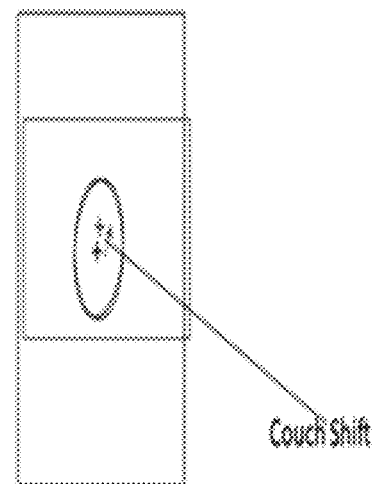

SYSTEMS AND METHODS FOR AUTOMATIC TREATMENT PLANNING AND OPTIMIZATION

FIELD

The present disclosure relates generally to radiation therapy, and more particularly, to systems, methods, and devices for automatically generating and optimizing radiation therapy treatment plans.

BACKGROUND

Radiation therapy involves medical procedures that use external radiation beams to treat pathological anatomies (tumors, lesions, vascular malformations, nerve disorders, etc.) by delivering prescribed doses of radiation (X-rays, gamma rays, electrons, protons, and/or ions) to the pathological anatomy, while minimizing radiation exposure to the surrounding tissue and critical anatomical structures.

In general, a full radiotherapy planning and treatment workflow includes several phases: a treatment planning phase, a treatment delivery phase, and a monitoring and evaluating phase in which the progress of the treatment, e.g., the dose accumulation is monitored.

In the treatment planning phase, first a precise three-dimensional (3D) map of the anatomical structures in the area of interest (head, body, etc.) is constructed using any one of (or combinations thereof) a computed tomography (CT), cone-beam CBCT, magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. This is followed by a prescription step, where a motion path for the radiation beam is computed to deliver a dose distribution that the radiation oncologist finds acceptable, considering a variety of medical constraints. Then, a team of specialists develop a treatment plan using special computer software to optimally irradiate the tumor and minimize dose to the surrounding normal tissue by designing beams of radiation to converge on the target area from different angles and planes. The treatment plan is then evaluated against the prescription.

In the treatment delivery phase, the radiation treatment plan is executed. During this phase, the radiation dose is delivered to the patient according to the prescribed treatment plan. Generally, a treatment plan is delivered to the patient over a series of radiation treatments referred to as fractions. There are many factors, however, such as, differences in a patient's setup position, changes that might occur if a patient's tumor regresses or if the patient loses weight during therapy, and uncertainties introduced by motion, for example, that can contribute to differences between the prescribed radiation dose distribution and the actual dose delivered (i.e., the actual dose delivered to the target during the radiation treatment). These anatomical and physiological changes can cause the target volumes and surrounding anatomical structures and organs to move and change in size and shape during the therapy. As such, executing or continuing to execute the initial treatment plan may result in an actual received dose distribution that differs from the planned distribution, and thus reduced doses to target volumes and/or increased doses to organs at risk (OARs). During the treatment delivery phase, therefore, the treatment plan may be adapted to the image of the day to better reflect the current situation. This involves making modifications to the initial treatment plan to match the new location and shape of the target volume and surrounding anatomical structures based on subsequently acquired image data.

Generating a treatment plan, whether it is the initial treatment plan generated during the treatment planning phase, or the adapted plan generated during the treatment delivery phase of an adaptive treatment workflow, can be time consuming and tedious.

Although some of the steps involved in the plan generation and plan adaptation process have been automated to assist and reduce the workload on the clinical user, it remains difficult to properly automate the optimization of the plan, especially in the field of intensity modulated radiation therapy (IMRT) and volumetric-modulated arc therapy (VMAT). Optimization is an iterative process where the user attempts to specify planning goals in the form of dose or biological objectives to create an ideal dose to target structures and minimize the dose to critical structures.

Optimization algorithms generally need a starting point (input metric) that specify the kind of dose distribution preferred. Generally, the starting point is either a set or a template of clinical goals (CG) to specify the preferred dose distribution (e.g., how much dose is needed for the target structure and what is the upper limit dose in an organ at risk), or a knowledge-based model that guides the optimization process (e.g., model estimates the achievable dose distributions per structure).

When both input metrics are present, however, the currently available automatic treatment optimization algorithms/processes provide dose distributions that satisfy neither inputs. There is a need therefore for a system and method to generate treatment plans in an automatic workflow that is capable of using multiple sources of clinical input data (i.e., input metrics), such as knowledge-based information and clinical goal templates.

Also, many currently available clinical goal settings/templates (CG) are missing information. As such, optimizing a treatment plan using a set of clinical goals (CG) as an input metric may provide dose distributions that are clinically unacceptable. In a standard, non-automatic workflow, the problem is bypassed by adding dose-volume objectives that shape and optimize dose distribution while fulfilling original goal metrics. In automatic planning, however, this cannot be applied. Therefore, there is a need for a system and method to automatically generate helping objectives derived from clinical goals to guide the automatic clinical goal-based dose optimization to output clinically acceptable treatment plans.

There are also situations where some of the clinical goals (CG) sorted by the user are incompatible with each other. Therefore, there is a need for a system and method that allows for automatic replacement of incompatible goals with compatible ones.

Further, in an adaptive therapy process, a treatment plan generated during treatment planning may need to be modified (adapted) during treatment delivery based on the image of the day. Generating and optimizing a new treatment plan is time consuming, however. In previous adaptive planning workflows, the adapting is done by either selecting a suitable plan from a pre-generated library of plans, where the adapting is done by translating a collimator opening or by scaling the total dose, or by selecting an existing plan and optimizing it using manual dose objectives as an input metric. Neither workflow allows, however, for automatic optimization of the adaptive treatment plan. There is a need therefore for a system and method to automatically optimize an adapted treatment plan in an adaptive workflow.

SUMMARY

Systems and methods are disclosed herein that are configured to automatically generate treatment plans based on an automatic workflow capable of using multiple sources of clinical input data (i.e., input metrics), such as knowledge-based information and clinical goal templates.

Systems and methods are described herein that are configured to automatically generate helping objectives derived from clinical goals to guide the automatic clinical goal-based dose optimization to output clinically acceptable treatment plans.

Systems and methods are described herein that are configured to automatically replace incompatible goals with compatible ones.

Systems and methods are also described herein that are configured to automatically generate and optimize an adapted treatment plan in an adaptive workflow.

Systems including a computer processing device configured to execute a sequence of programmed instructions embodied on a computer-readable storage medium, the execution thereof causing the system to execute the method steps disclosed herein, are also disclosed.

A non-transitory computer-readable storage medium upon which is embodied a sequence of programmed instructions for the generation of day to day treatment images to be used in adaptive radiation therapy, and a computer processing system that executes the sequence of programmed instructions embodied on the computer-readable storage medium are also disclosed. Execution of the sequence of programmed instructions can cause the computer processing system to execute the automatic treatment planning and optimization processes described herein.

Objects and advantages of embodiments of the disclosed subject matter will become apparent from the following description when considered in conjunction with the accompanying drawings.

BRIEF DESCRIPTION OF DRAWINGS

FIG. 18 is a process flow diagram for determining a treatment isocenter, according to various embodiments of the disclosed subject matter.

DETAILED DESCRIPTION

Figure 1:
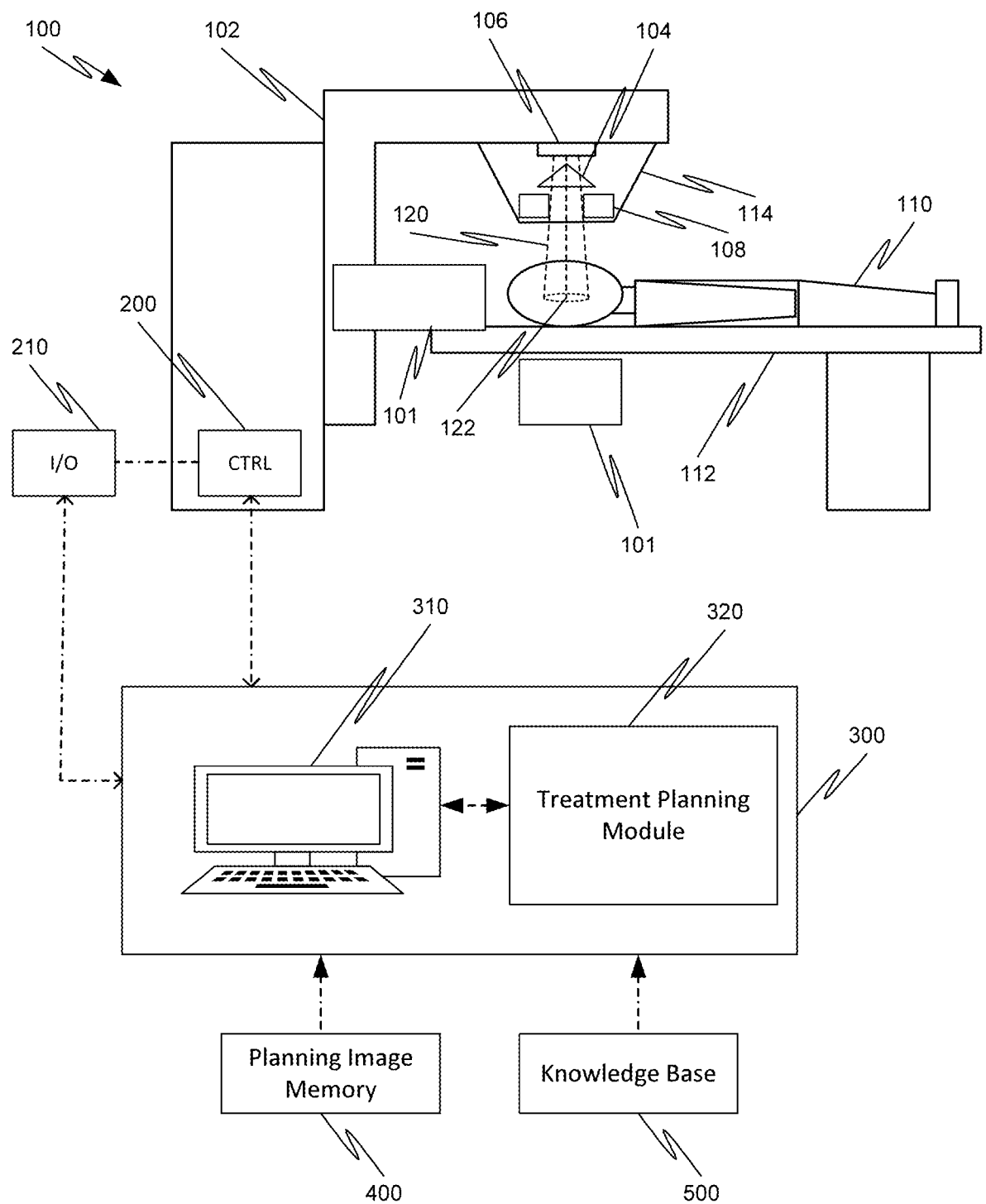
FIG. 1 is a simplified schematic diagram of a radiation therapy system, according to various embodiments of the disclosed subject matter.
Figure 2:
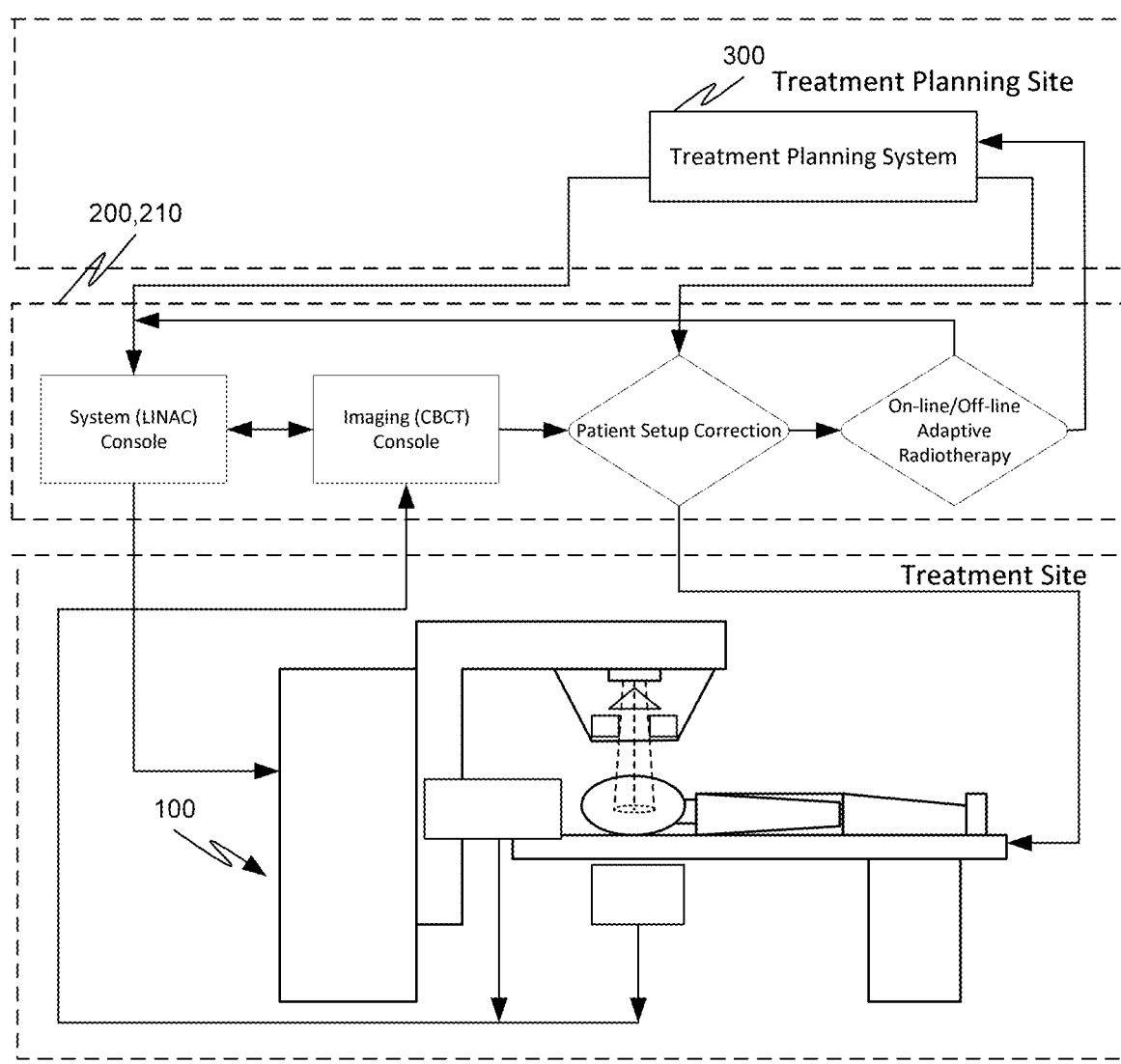
FIG. 2 is a simplified illustration for using the radiation therapy system of FIG. 1 for on-couch adaptive radiation therapy, according to various embodiments of the disclosed subject matter.

Referring to FIG. 1, an exemplary radiation therapy system 100 is shown that can be used in adaptive radiation therapy as shown in FIG. 2, and which can deliver radiation in accordance with treatment plans that are determined using techniques described herein. The radiation therapy system 100 can provide radiation to a patient 110 positioned on a treatment couch 112 and can allow for the implementation of various radiation dose verification protocols. The radiation therapy can include photon-based radiation therapy, particle therapy, electron beam therapy, or any other type of treatment therapy.

In an embodiment, the radiation therapy system 100 can include a radiation treatment device 101 such as, but not limited to, a LINAC operable to generate one or more beams of megavolt (MV) X-ray radiation for treatment. The LINAC may also be operable to generate one or more beams of kilovolt (kV) X-ray radiation, for example, for patient imaging. The system 100 has a gantry 102 supporting a radiation treatment head 114 with one or more radiation sources 106 and various beam modulation elements, such as, but not limited to, flattening filter 104 and collimating components 108. The collimating components 108 can include, for example, a multi-leaf collimator (MLC), upper and lower jaws, and/or other collimating elements. The collimating components 108 and/or the flattening filter 104 can be positioned within the radiation beam path by respective actuators (not shown), which can be controlled by controller 200.

The gantry 102 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 114 at various rotational and/or axial positions relative to the patient 110 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 108, which can be a computer-controlled mechanical beam shaping device attached to the head 114 and includes an assembly of metal fingers or leaves. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)).

Alternatively, or additionally, the radiation therapy device 101 can be a tomotherapy device, a helical tomotherapy device, or a simplified intensity modulated arc therapy (SIMAT) device, a volumetric modulated arc therapy (VMAT) device, or a volumetric high-definition (or hyperarc) therapy (HDRT). In effect, any type of IMRT device can be employed as the radiation therapy device 101 of system 100, and can also include an on-board volumetric imaging, which can be used to generate in-treatment image data generated during a treatment session.

Each type of radiation therapy device can be accompanied by a corresponding radiation plan and radiation delivery procedure.

The controller 200, which can be, but is not limited to, a graphics processing unit (GPU), can include a computer with appropriate hardware such as a processor, and an operating system for running various software programs and/or communication applications. The controller 200 can include software programs that operate to communicate with the radiation therapy device 101, which software programs are operable to receive data from external software programs and hardware. The computer can also include any suitable input/output (I/O) devices 210, which can be adapted to allow communication between controller 200 and a user of the radiation therapy system 100, e.g., medical personnel. For example, the controller 200 can be provided with I/O interfaces, consoles, storage devices, memory, keyboard, mouse, monitor, printers, scanner, as well as a departmental information system (DIS) such as a communication and management interface (DICOM) for storing and transmitting medical imaging information and related data and enabling the integration of medical imaging devices such as scanners, servers, workstations, printers, network hardware, etc.

Alternatively, or additionally, the I/O devices 210 can provide access to a network (not shown) for transmitting data between controller 200 and remote systems. For example, the controller 200 can be networked via I/O 210 with other computers and radiation therapy systems. The radiation therapy system 100, the radiation treatment device 101, and the controller 200 can communicate with a network as well as databases and servers, for example, a dose calculation server (e.g., distributed dose calculation framework) and a treatment planning system 300. The controller 200 may also be configured to transfer medical image related data between different pieces of medical equipment.

The system 100 can also include a plurality of modules containing programmed instructions (e.g., as part of controller 200, or as separate modules within system 100, or integrated into other components of system 100), which instructions cause system 100 to perform different functions related to adaptive radiation therapy or other radiation treatment, as discussed herein, when executed. For example, the system 100 can include a treatment plan module operable to generate the treatment plan for the patient 110 based on a plurality of data input to the system by the medical personnel, a patient positioning module operable to position and align the patient 110 with respect to a desired location, such as the isocenter of the gantry, for a particular radiation therapy treatment, an image acquiring module operable to instruct the radiation therapy system and/or the imaging device to acquire images of the patient 110 prior to the radiation therapy treatment (i.e., pre-treatment/reference images used for treatment planning and patient positioning) and/or during the radiation therapy treatment (i.e., in-treatment session images), and to instruct the radiation therapy system 100 and/or the imaging device 101 or other imaging devices or systems to acquire images of the patient 110.

The system 100 can further include a radiation dose prediction module operable to predict a dose to be delivered to the patient 110 before commencement of the radiation treatment therapy, a dose calculation module operable to calculate the actual dose delivered to the patient 110 during radiation therapy treatment, a treatment delivery module operable to instruct the radiation therapy device 100 to deliver the treatment plan to the patient 110, a correlation module operable to correlate the planning images with the in-treatment images obtained during radiation therapy, a computation module operable to reconstruct three-dimensional target volumes from in-treatment images, an analysis module operable to compute displacement measurements, and a feedback module operable to instruct the controller in real-time to stop radiation therapy based on a comparison of the calculated displacement with a predetermined threshold value (range).

The system 100 can further include one or more contour generation modules operable to generate contours of target volumes and other structures in pre-treatment (planning, reference) and in-treatment (treatment session) images, an image registration module operable to register pre-treatment images with subsequent in-treatment images, a dose calculation module operable to calculate accumulated dose, a contour propagation module operable to propagate a contour from one image to another, a contour verification module operable to verify a generated contour, a registration deformation vector field generation module operable to determine deformation vector fields (DVFs) as a result of an image deformation process. The system 100 can further include modules for electron density map generation, isodose distribution generation, does volume histogram (DVH) generation, image synchronization, image display, treatment plan generation, treatment plan optimization, automatic optimization parameter generation, updating and selection, and adaptive directives and treatment information transfer. The modules can be written in the C or C++ programming language, for example. Computer program code for carrying out operations as described herein may be written in any programming language, for example, C or C++ programming language.

Automatic Treatment Plan Generation

The treatment planning system 300 can be used to generate treatment plans for the radiation therapy system 100, based on image data, such as CT or CBCT image data saved in a storing device 400, for example. In a typical planning process, qualified medical personnel (physician) manually draw contours on one or more of the initial reference planning images. These contours delineate the malignant tumor that is to be irradiated, as well as one or more other structures, such as organs, tissue, etc. that are susceptible to substantial damage from radiation exposure. The planning images can also be semi-automatically segmented to delineate the malignant tumor that is to be the target of the irradiation, and any surrounding critical structures (OARs) whose irradiation should be limited. Typical delineations for the malignant tumor include the gross target volume (GTV), the clinical target volume (CTV), and the planning target volume (PTV). The (GTV) determines the anatomic region which harbors the highest tumor cell density and requires the highest prescribed dose. The (GTV) is the position and extent of the gross tumor, i.e. what can be seen, palpated or imaged. The (CTV) contains the (GTV), plus a margin for sub-clinical disease spread which therefore cannot be fully imaged. The (CTV) is the volume that must be adequately treated to achieve cure. The (PTV) allows for uncertainties in planning or treatment delivery. It is a geometric concept designed to ensure that the radiotherapy dose is actually delivered to the (CTV). The (PTV) is thus used to compensate for treatment setup uncertainties through volumetric expansion of the (CTV) margins. The reference/planning images can also illustrate soft tissues, influencer structures, organs, blood vessels, bones, etc.

Once the physician generates a list of treatment parameters, such as but not limited to, the targets for which the radiation is to be maximized, organs and healthy tissue regions for which the radiation is to be minimized, a treatment plan is generated that also takes into consideration constraints imposed on the treatment process by the radiation therapy system 100 used for delivering the radiation to the patient. Additionally, or alternatively, the treatment planning system 300 can use information from other imaging modalities, such as MRI, PET, etc., and/or other image data for generating the treatment plans. The treatment plan is then reviewed by the physician to ensure that it meets the clinical needs of the patient.

Automatic treatment planning follows two general approaches/techniques. The first approach (i.e., goal-based approach) is to develop an automatic optimization algorithm to automatically adjust optimization model parameters for a new patient to generate a satisfactory plan that meets some predetermined clinical criteria. In the goal-based approach, to get the dose distribution that fulfills the predetermined clinical criteria, an optimization algorithm is used with a cost function defined for the dose distribution (i.e., mathematical model representing the dose objectives). Plan optimization then requires the minimization of the cost function, and the treatment plan is the solution that minimizes the cost function. Plan optimization can include a series of sub-optimizations, each minimizing a defined cost function. The cost functions may be defined using dose objectives but may also be defined using objectives that are not dose objectives, such a monitor units (MU), for example.

In the goal-based approach, the starting point for the optimization algorithm specifying a preferred dose distribution is a set or a template of clinical goals (CG). Radiation therapy requires that the physician prescribe suitable goals of radiation doses for the treatment of the patient. These clinical goals (CG) can be given for example in the form of mean dose of radiation (in Gray) to a target structure and the dose that certain volume of an organ, such as an organ at risk (OAR), must not exceed. Clinical goals, however, may also be given in other dimensions that are not in the form of dose of radiation to a target structure and dose to volume of organ. Each of the given goals can further be ordered in priority describing the importance of meeting a goal in comparison to another goal. Such a set is referred to as a prioritized set of clinical goals (prioritized CG). Each clinical goal can be expressed as a quality metric Q and its associated goal value. An exemplary prioritized set of clinical goals is:

GOAL 1: Target (PTV) must receive 50 Gy: Priority 1
GOAL 2: Organ at risk X (OARx) must receive less than 25 Gy: Priority 2
GOAL 3: Organ at risk Y (OARy) must receive a mean dose of less than 30 Gy: Priority 3

A cost function ($C_G$) defining the dose distribution for such a set of prioritized clinical goals (CG) can be, exemplarily, expressed as:

$$C_G = w_{P1}(D_{PTV} - GL_{PTV})^2 + w_{P2}(D_x - GL_x)^2 + w_{P3}(D_y - GL_y)^2 \quad (1)$$

where $w_{Pi}$ is a weighting factor for the priority i, D is the current dose in the target structure/organ, and GL is the goal dose in that target structure/organ. This cost function ($C_G$) is exemplary only, and the cost function can take on many different forms, including cost functions where the clinical goals are not expressed as dose-volume objectives. For example, in a case where plan optimization includes a series of sub-optimizations, each minimizing a defined cost function using dose objectives, the results of the sub-optimizations can be continuously evaluated against quality values of the clinical goals. In such a case, the cost function form can be continuously altered for the next sub-optimization. This allows for the clinical goals to be expressed differently than dose-volume objectives. An exemplary clinical goal that is not expressed as a dose-volume objective is the incoming radiation (fluence) pattern, for example.

Regardless of how the cost function is expressed, in the goal-based approach, once the cost function is expressed, a treatment plan candidate can be generated by minimizing the cost function ($C_G$). There are many algorithms that can be applied to minimize a cost function, including but not limited to, calculating the gradient of the cost function.

The second approach (i.e., knowledge-based approach) is to employ a library of clinically approved and delivered plans of previously treated patients with similar medical characteristics in order to find a set of parameters for a new patient that produces a clinically desirable plan. In this approach, an algorithm (i.e., a Dose Volume Histogram (DVH) model, for example) that has been trained from historical patient data (i.e., structures and dose distributions) is used as a starting point to predict the achievable dose distributions for a new set of patient structures. The achievable dose distributions are presented as a pair of Dose Volume Histograms (DVHs) representing the lower and upper bounds of the 95% confidence interval of the prediction. These DVH histograms can then be used as objectives (i.e., line objectives, for example) for each structure. A cost function $C_K$ for a knowledge-based approach can therefore exemplary be expressed as:

$$C_K = (DVH_{PTV} - LO_{PTV})^2 + (DVH_x - LO_x)^2 + (DVH_y - LO_y)^2 \quad (2)$$

where DVH is the current dose volume histogram curve for the target structure/organ, and LO is the line objective curve for that target structure/organ.

In a situation where both a template of prioritized clinical goals (CGs) as well as knowledge-based models are present as input metrics to the optimization algorithm, in order to generate a treatment plan that satisfies both inputs, an appropriate cost function needs to be determined.

Figure 3:
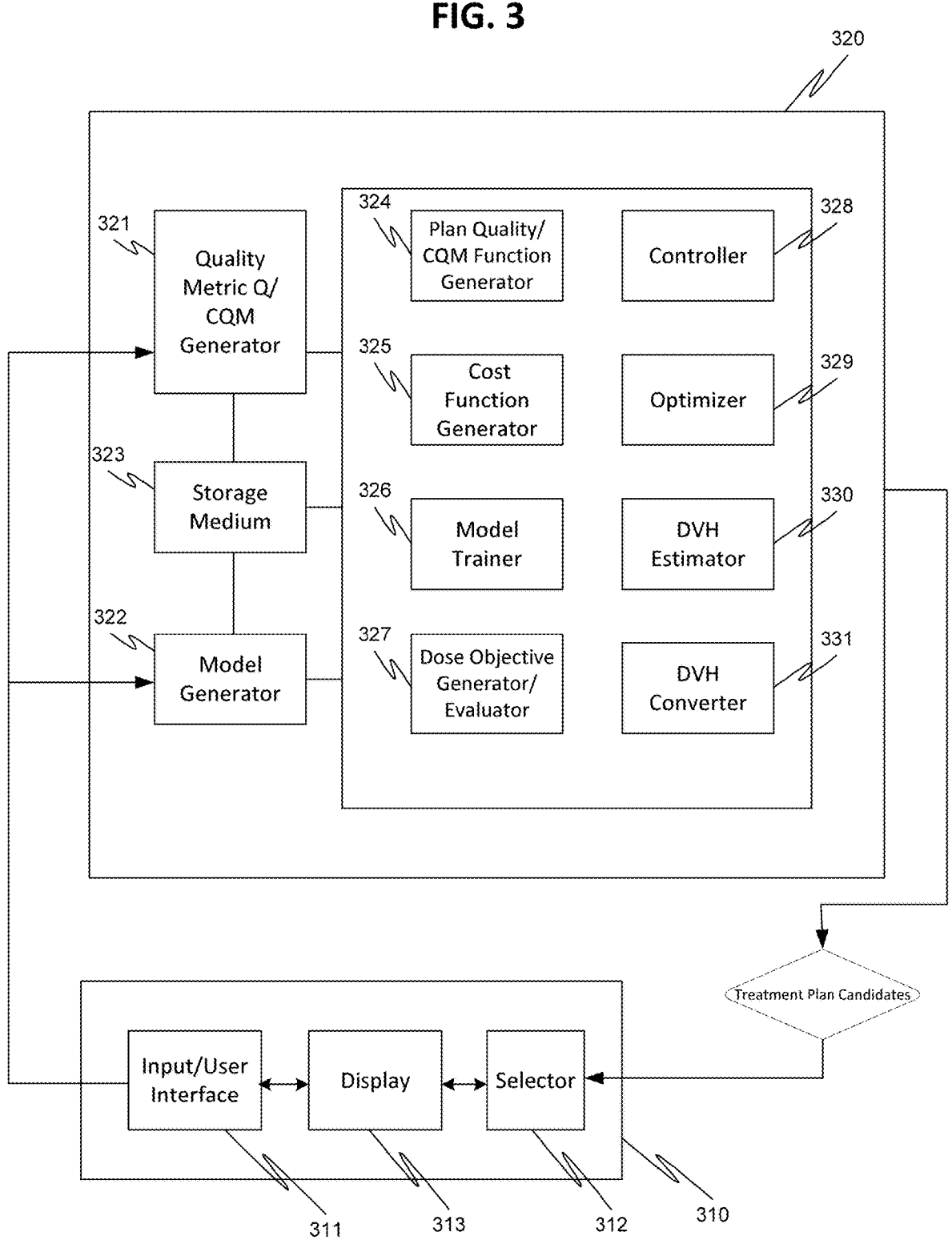
FIG. 3 is a schematic illustration of a treatment planning module for use in a treatment planning device, according to various embodiments of the disclosed subject matter.

FIG. 3 illustrates a treatment planning system 300 configured to generate treatment plans based on clinical data of different input sources, such as a first data source that includes prioritized clinical goals (CGs) as the first set of clinical data, and a second data source that includes knowledge-based information, such as a knowledge-based model, as the second set of clinical data. The treatment planning system 300 includes at least one processor 310 having an input/user interface 311, a display device 313, and optionally, a separate selector 312, and a treatment planning module 320. Although illustrated as a separate selector 312, the selector can be a part of the input/user interface.

The treatment planning module 320 includes program memories that contain processor executable instructions that, when executed by the processor 310, generate treatment plan candidates and associated treatment plans that can be executed by a processing unit (e.g., controller 200) of the radiation therapy system 100. The treatment planning module 320 includes a plurality of modules (321-331) contributing to the generation of the treatment plan candidates and ultimately the treatment plans.

The treatment planning system 300 is configured to communicate with the planning image memory 400 containing image data, and with a knowledge base 500 which is a database or other information retrieval system that contains plan templates including clinical goals (CGs) and priorities for different anatomical structures, as well as knowledge-based information such as patient records (i.e., previous/existing treatment plans) that are similar to the current patient record, treatment types, and knowledge-based statistical models, such as DVH models, for example.

In order to generate treatment plans based on both types of inputs, a total cost function $C_{Total}$ is generated that is a weighted combination of the objectives of the goal-based approach (i.e., goal objectives) and the objectives of the knowledge-based approach (i.e., line objectives). The total cost function $C_{Total}$ can be expressed as:

$$C_{Total} = C_G + mC_K \quad (3)$$

where m is a weighting factor that can be changed by a user via the user interface 311. The higher the value of the weighting factor m, the more weight is given to the line objectives of the knowledge-based approach. For example, for m=10%, more weight is given to the goal objectives of the goal-based approach, whereas, for m=90%, more weight is given to the line objectives of the knowledge-based approach. Different treatment plan candidates can thus be generated using different values for the weighting factor m.

The total cost function $C_{Total}$ can also be expressed in terms of the different sets of objectives, taking into account the priority order of the clinical goals:

$$C_{Total} = C_G + aw_{P1}(DVH_{PTV} - LO_{PTV})^2 + bw_{P2}(DVH_x - LO_x)^2 + cw_{P3}(DVH_y - LO_y)^2 \quad (4)$$

where the priority weighting factors $w_{P1}$ from eq. (1) are applied to the line objective costs in eq. (2), and are combined with strategy-weighting factors a, b and c, which can be used to generate different types of treatment plans. For example, a goal-weighted plan candidate could use a=0.1, b=0.08, and c=0.07, whereas, a plan candidate which is weighted toward the knowledge-based plan could use a=0.9, b=0.08, and c=0.7, for example.

Exemplary ways to obtain each of the cost functions $C_G$ and $C_K$ are described in detail below.

To obtain the cost function $C_G$, a quality metric generator 321 generates a quality metric $Q_i$ for each of the goals in the set of prioritized clinical goals ($C_G$) obtained via the user interface 311. Examples of quality metrics ($Q_i$) are: Target (PTV) must receive 50 Gy, Organ at risk X (OARx) must receive less than 25 Gy, Organ at risk Y (OARy) must receive a mean dose of less than 30 Gy, spine max dose being less than 50 Gy, relative (PTV) volume getting less than prescription dose is less than 5% Gy, etc. In the treatment planning system 300, a same quality metric $Q_i$ may appear in multiple different goals if associated to different goal values. Also, the treatment planning may involve multiple clinical goals represented as different respective quality metrics Q with corresponding clinical goal values. The priorities of the clinical goals are represented by prioritization metric values (0, 1, 2, etc.), with a smaller prioritization metric value indicating that the priority is more important.

From the individual quality metrics $Q_i$, the plan quality can be deducted by assigning a quality metric dependent plan quality, meaning that a user may define what would be the plan quality if only one of the quality metrics is evaluated. The total plan quality can be generated by a plan quality generator 324 as a function of the individual quality metric dependent plan qualities. The total plan quality may then represent the cost function $C_G$. This cost function $C_G$ mathematically represents the objectives $O_G$ for a preferred dose-distribution in a goal-based approach.

Alternatively, each of the clinical goals may be represented as a continuous quality metric (CQM), in which case, the plan quality may be defined as a continuous function G, that is derived from continuous functions $G_i$ (i.e., Q-functions) associated with the quality metrics $Q_i$. A continuous function $G_i$ describes a quality metric $Q_i$ in more detail. For example, a continuous function $G_i$ may be configured to influence when a desired value (Q-value) of a corresponding quality metric $Q_i$ is to be achieved during the optimization. Alternatively, or additionally, a continuous function $G_i$ may be configured to influence how fast a desired value of a quality metric $Q_i$ is to be achieved relative to another quality metric Q and/or relative to another desired value of the quality metric $Q_i$. Alternatively, or additionally, a continuous function $G_i$ may be configured to influence how an optimizer 329 is to treat a quality metric $Q_i$ after its desired value has been achieved during optimization.

The continuous functions $G_i$ may be generated by the quality metric generator 321. Alternatively, the continuous functions $G_i$ may be defined by a user via the user interface 311 by allowing the user to enter different parameters to define each of the functions. Alternatively, the user interface 311 may allow the user to select a desired continuous function from a list of previously formed continuous functions, and/or to modify the selected continuous functions for a particular patient. Alternatively, the quality metric generator 321 may be configured to automatically generate continuous functions $G_i$ for each of the user-defined clinical goals.

The total plan quality function G is then obtained from the individual continuous functions $G_i$. For example, the function G may be defined as a minimum of all the individual continuous functions $G_i$. Alternatively, the function G may be defined as one that minimizes the difference to individual plan qualities calculated from the individual continuous functions $G_i$. Alternatively, the function G may be defined as the one minimizing the aberrations to different quality metric scorings.

The total plan quality function G may represent the cost function $C_G$. This cost function $C_G$ mathematically represents the objectives $O_G$ for a preferred dose-distribution in a goal-based approach.

The generation of quality metrics $Q_i$, continuous quality metrics (CQM), continuous quality functions $G_i$ (Q-functions), individual plan qualities, total plan quality, and continuous plan quality functions G's are described in detail in U.S. patent application Ser. No. 16/237,489, filed Dec. 31, 2018, and assigned to Varian Medical Systems International AG, which is incorporated herein by reference in its entirety.

In order to generate the cost function $C_K$, on the other hand, the treatment planning module 320 obtains, via the user interface 311, knowledge-based information, including one or more, or a combination of, a selection of treatment plans from the list of existing treatment plans, patient geometry, identity of the target structure, and identities of the organs at risk (OARs), as well as one or more of dose distribution models that were previously developed following desirable clinical practices. The treatment planning module 320 may further obtain via the user interface 311 input defining or affecting how a dose-distribution model may be generated for a new patient.

The existing treatment plans including treatment parameters and/or the previous models used to develop these treatment plans may be stored in the knowledge base 500. Alternatively, they may be stored in a storage medium 323. Alternatively, they may be stored in a separate storage device and be communicated to the treatment planning module 320 through wired or wireless connection via the storage medium 323.

In some embodiments, the treatment planning module 320 may require a minimum number of existing treatment plans for the current patient dose-distribution model creation by a model generator 322. For example, models created for certain anatomical regions, such as head or neck, may require more than a minimum number of plans. The model generator 322 may obtain any number of previous/existing treatment plans required for the generation of a robust model. The existing treatment plans may be selected as the ones that have the same OAR structure as those for the current/new patient.

The existing/previous treatment plans are used as baseline for the model trainer 326 of the treatment planning module 320 to define a trained dose-distribution model for the current/new patient. In some embodiments, the trained model is a DVH estimation model. The model trainer 326 is configured to perform plan and patient data modeling including data extraction from the clinical database 500 and subsequent model training. The trained model takes into account the current/new patient's anatomy and planning objectives. The training of the DVH estimation model generates mathematical parameters through principal component and regression models, for example, relating the geometric and dosimetric features, to be used by a DVH estimator 330 to estimate Dose-Volume Histograms (DVHs) for the current/new patient based on the plan and patient data modeling.

The model trainer 326 can use various available methodologies to train the DVH estimation models, such as, but not limited to, parametrization of the structure set and dose matrices for the existing treatment plans. The parametrization identifies the acceptable clinical trade-offs, including trade-offs for target coverage and dose to the OARs, and analyzes the calculated DVH, the distance-to-target histogram (DTH), and the anatomical features (i.e., relative overlap volume, relative out-of-field volume, absolute OAR volume, absolute target volume, etc.). Any other available model trainer methodologies can be used to train the model, however.

The model trainer 326 may also be configured to generate and provide a statistical summary about the goodness of the model as an output of the training phase, which can then be used as a model trainer evaluation. A metric may also be provided that measures the distance between the original DVH and the mean of the upper and lower bounds of the estimated DVH.

The trained DVH estimation model is then applied to a new case, i.e., the new patient, by the DVH estimator 330 to generate the DVH estimates for the new patient. The DVH estimates may be presented in the form of bands that mark the upper and lower bounds to be achieved by the optimizer 329 during optimization. The DVH estimator 330 may also be configured to generate the most probable upper and lower bound DVHs using a PCA-regression model or a mean and standard deviation model, for example.

An objective generator 327 then determines the dose volume constraints (as line objectives LO and/or point objectives) based on the DVH estimates obtained by the DVH estimator 330. These objectives (line objectives, for example) can be converted into one or more cost functions $C_K$ by the objective generator 327. In an embodiment, the cost function $C_K$ mathematically represents the line objectives $O_L$ for a preferred dose-distribution using the knowledge-based approach.

The objective generator 327 is further configured to set target objectives based on prescription and user-defined coverage of the target structure, and/or to determine optimization objectives and their priorities.

Alternatively, or additionally, optimization objectives and their priorities may be added by a user via the user interface 311. Alternatively, or additionally, line objectives LO, upper objectives, lower objectives, mean objectives, or any combination of these, and their respective priorities may be selected for each structure in the model. Alternatively, or additionally, the priorities may be manually defined by a user via the user interface 311 or may be calculated based on the DVH estimates and target prescriptions.

Alternatively, or additionally, the user may add further objectives to the cost function $C_K$ and modify priorities if needed and/or desired, prior to optimization.

The total cost function $C_{Total}$ can then be generated in a cost function generator 325. The total cost function $C_{Total}$ can be expressed as the sum of the weighted individual cost functions $C_G$ and $C_K$, or the weighted sum of the goal-based objectives (i.e., first set of objectives) and the line-based objectives (i.e., second set of objectives), as indicated in eqs. (3) or (4).

After the total cost function $C_{Total}$ is obtained, the optimizer 329 may perform treatment planning optimization to determine a plurality of treatment plan candidates based on the total cost function $C_{Total}$. The optimizer 329 may perform optimization by minimizing the total cost function $C_{Total}$ using any appropriate minimization technique. For example, the optimizer 329 may be configured to determine an initial solution S; calculate dose D based on the initial solution S; obtain total cost function $C_{Total}$; calculate a gradient of the total cost function $C_{Total}$ around dose D; project the gradient of the total cost function $C_{Total}$ into a solution space to obtain gradient of S; and determine a new solution S' based on the initial solution S and the gradient of S. The optimizer 329 is further configured to repeat these steps until a solution converges.

By giving different values to the weighting factor (m) in the total cost function $C_{Total}$ defined in eq. (3), the optimizer 329 is configured to generate a plurality of treatment plan candidates to be presented to a user on display 313, for selection using selector 312. A first treatment plan candidate, for example, may be generated for a weighting factor (m) of 10%. A weighting factor of 10% indicates a goal-weighted plan, meaning that this first treatment plan candidate is giving more weight (i.e., 90%) to the objectives of the goal-based approach. Similarly, a weighting factor (m) of 90%, for example, indicates a knowledge-based weighted plan, meaning that a second treatment plan candidate is given more weight to the knowledge-based objectives of the knowledge-based approach.

When the weighting factor (m) is expressed as the prioritized combination of priority weighting factors $w_{Pi}$ and the strategy weighting factors a, b and c, picking different values for factors a, b, and c can be used to generate different types of plans. The values used for the weighting factor (m), and similarly the values for the strategy factors a, b, and c, are exemplary only, and any other values and/or combination of values may be used to generate differently weighted treatment plan candidates.

The solution to the optimization process by the optimizer 329 results in treatment parameters being determined for the treatment plan candidates. By optimizing different treatment plan candidates, different treatment plan options can be given to the user to select from. The treatment plans can be stored in a storage device of the treatment planning system 300, to be later retrieved by the radiation treatment system 100 for operating the treatment system 100 to deliver radiation treatment according to a chosen radiation treatment plan.

Although specific expressions for the individual cost functions $C_G$ and $C_K$ were used herein, it is to be understood that these expressions are exemplary only, and that the automatic optimization described throughout the specification is configured to use a cost minimization function to solve a sub-problem in the form of a cost function that takes into account different sources of information to obtain plan candidates in its search of a best plan quality.

To optimize the treatment plans, at the outset of the treatment planning process, a number of control points (CPs) are specified for the beam trajectory that takes into consideration the beam shaping elements of the radiation treatment system 100. Each control point (CP) is associated with a set of treatment parameters, including but not limited to, a set of (MLC) leaf positions, (MLC) shape, gantry rotation speed, gantry position, dose rate, and/or any other parameters. The number and position of the control points (CPs) may be set in any convenient manner, such as, but not limited to, by using the treatment planning software, or by the system operator. In an exemplary embodiment, the beam trajectory can include a single 180 degrees arc trajectory and approximately 177 sequential control points (CPs), which means that there are 177 configurations that the LINAC should conform to in order to deliver the planned treatment. Based on the treatment parameters, a dose distribution within the treatment volume can be calculated for each control point (CP) by any number of techniques, such as, but not limited to, pencil beam convolution, or any other suitable algorithm, and the radiation dose distribution for each (CP) can be associated with the corresponding gantry angle, (MLC) configuration, and monitor unit (MU). As such, during treatment delivery, the extracted (CP) parameters can be associated with corresponding calculated dose distributions for each (CP).

Figure 4:
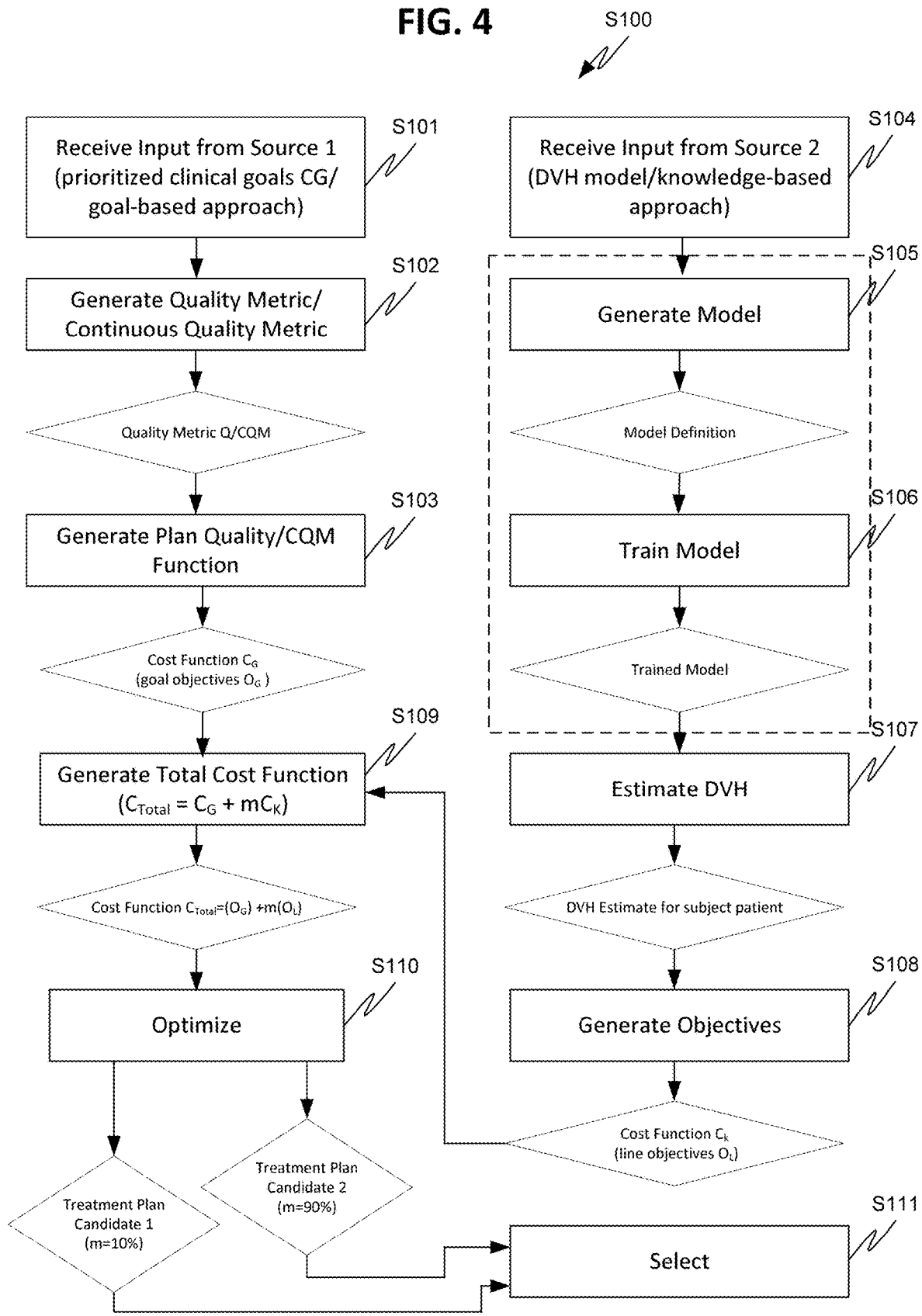
FIG. 4 is a process flow diagram for automatic treatment planning using multiple clinical data sources, according to various embodiments of the disclosed subject matter.

FIG. 4 illustrates a process S100 for generating a plurality of treatment plan candidates based on clinical input data of two different input sources received from a user via the user interface 311. In Step S101, the treatment planning module receives the prioritized set of clinical goals via a user interface. In Step S102, quality metrics or continuous quality metrics are generated for the prioritized clinical goals. A quality plan or a quality plan function is next generated in Step S103 to obtain the objectives $O_G$ of the goal-based approach.

In Step S104, the treatment planning module 302 receives knowledge-based information including information regarding previous treatment plans, dose-distribution models used for the previous treatment plans, and new patient information. A DVH model is generated from the knowledge-based information in Step S105, and the DVH model is trained in Step S106. The trained model is applied to the new patient data to generate DVH estimates in Step S107. From the DVH estimates, the objectives of the knowledge-based approach are obtained in Step S108. The cost function $C_K$ represents the set of line objectives of this knowledge-based approach.

Although the model generation and training steps S105 and S106 are illustrated in FIG. 4, it is to be understood that these steps can be separately performed prior to the optimizing, and the resulting trained DVH estimation model saved in the storage medium 323, for example, for later use. During optimization, it is this saved trained DVH estimation model that constitutes the knowledge-based information inputted from the second source (i.e., knowledge-based approach), which is then automatically applied to a new patient to generate the DVH estimates. This previously generated trained DVH estimation model thus includes all pertinent information regarding the earlier plans.

The total cost function $C_{Total}$ is obtained in Step S109 by adding the set of objectives of the goal-based approach ($O_G$) to the set of objectives of the knowledge-based approach ($O_L$), where the second set of objectives include a weighting factor (m). Alternatively, each objective in the second set of objectives can have its associated weighting factor (a, b, c, etc.) that takes into consideration the relative priorities of the first set of objectives.

In Step S110, two treatment plan candidates are generated by optimizing the total cost function $C_{Total}$. A first treatment plan candidate includes a weighting factor (m) of 10%, for example, and a second treatment plan candidate includes a weighting factor (m) of 90%, for example. A user may then select in Step S111, a treatment plan candidate that best reflects a desired outcome.

Figure 5:
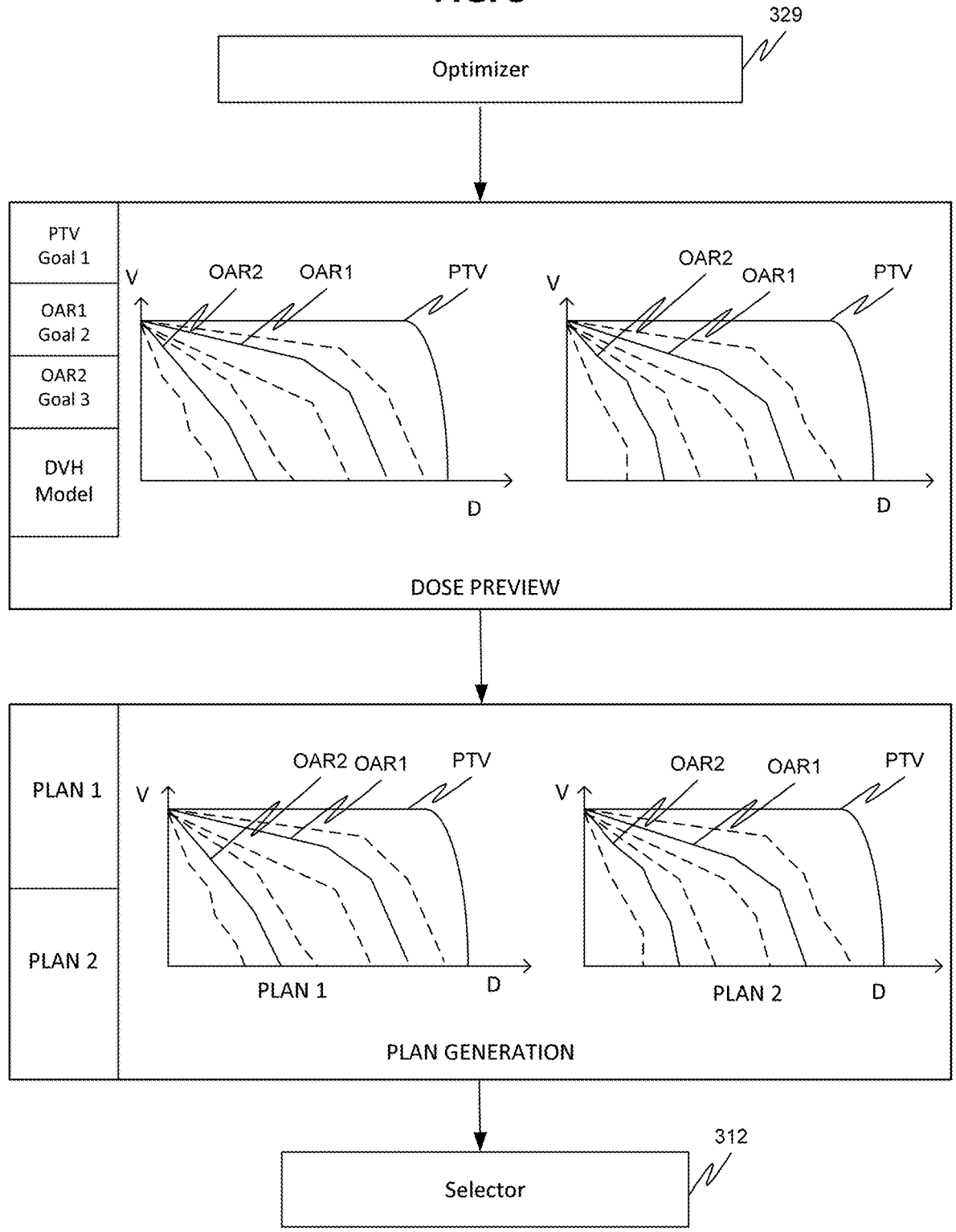
FIG. 5 is an illustration of a display and selection of treatment plan candidates, according to various embodiments of the disclosed subject matter.

Exemplary treatment plan candidates are illustrated in FIG. 5. During dose preview and plan selection, a user may review the dose distribution and treatment plan candidates obtained for different weighting factors (m) and select the treatment plan that best represents the desired treatment outcome. The selected treatment plan can be stored in a storage device of the processor 310 to be implemented as a plan to treat a patient in the radiation therapy system 100.

Additionally, after a treatment plan has been developed in the treatment planning system 300, and before the treatment plan is executed by an adaptive radiation therapy system shown in FIG. 2, the physician can develop a set of adaptive directives, which is a list of parameters/directives/information that describes the intent of the adaptive treatment, namely, the 4D description of the planned treatment for the patient. The set of adaptive directives can include information regarding the planned dose specification (i.e., Rx prescription), whether adaptive or standard IGRT therapy is to be used, the prescribed clinical goals (CGs), such as but not limited to, the target dose coverage and (OAR) risk dose limits, the clinical goal values (CGs), the plan quality values, the overall plan quality value, the planning image, such as but not limited to a CT image, supporting images with their corresponding registration information (PET, MRI, etc.), the planned patient model (i.e., the contours of the structures, such as the target volumes, OARs and other structures on the planned image), the treatment plan 3D dose (i.e., RT 3D dose), a list of the structures (target volumes, OARs, etc.), information regarding the shapes and location of the planned structures on the planned image, as well as information regarding the optimization of the treatment plan, such as the gantry angle, (MLC) configuration, and the monitor unit (MU) for each control point (CP).

Converting DVH Estimates into Clinical Goals

Another way to generate treatment plans based on clinical input data from different input sources, is to convert the DVH estimates obtained in the knowledge-based approach into clinical goals (converted clinical goals), and use these converted clinical goals together with the original set of prioritized clinical goals of the first input source to generate a cost function to be optimized.

Figure 6:
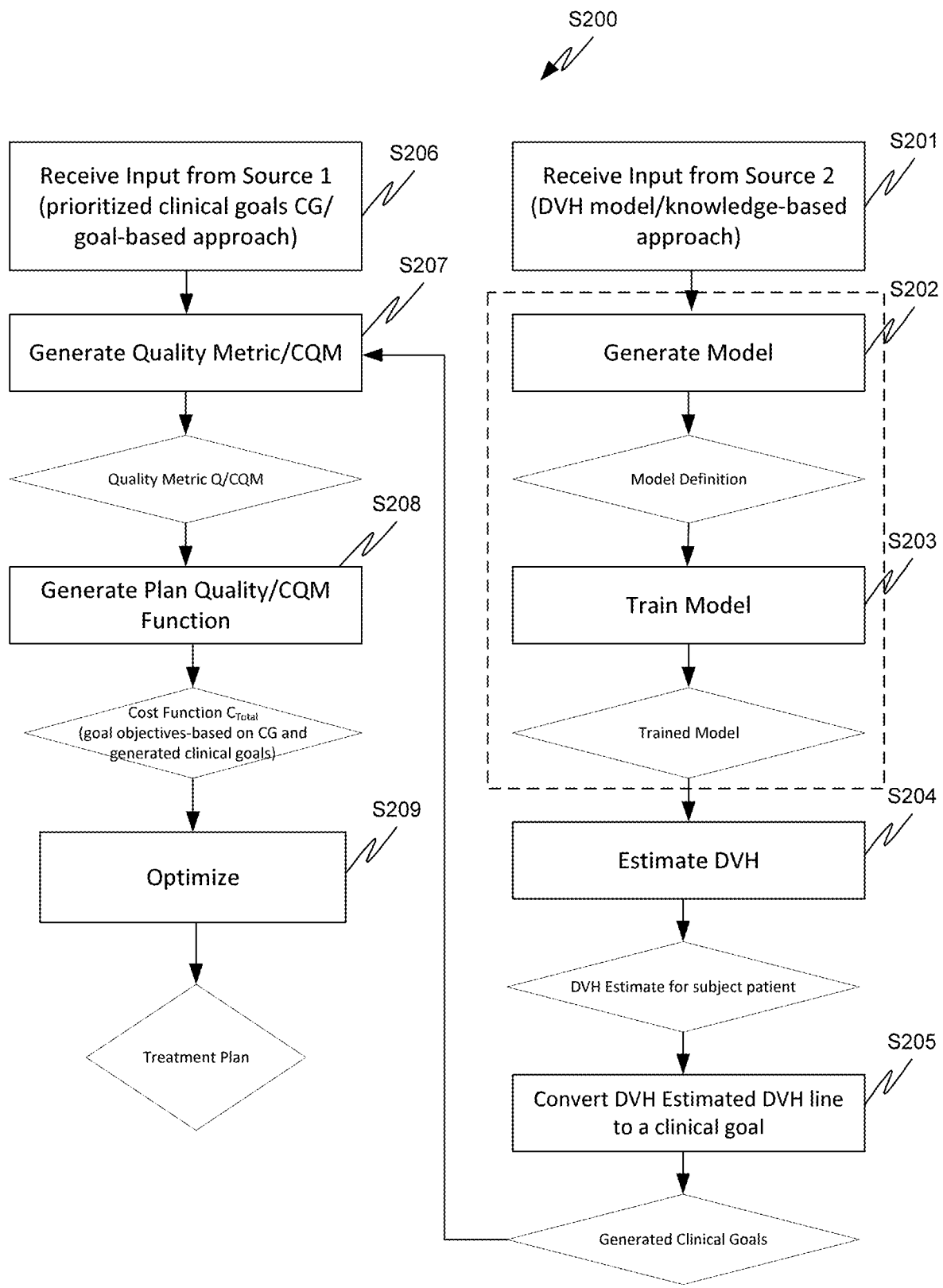
FIG. 6 is a process flow diagram for automatic treatment planning using clinical goals converted from DVH estimates, according to various embodiments of the disclosed subject matter.

FIG. 6 illustrates a process S200 by which a treatment plan can be generated based on clinical input data of two different input sources received from a user via the user interface 311. In Step S201, the treatment planning module 302 receives knowledge-based information including information regarding previous treatment plans, dose-distribution models used for the previous treatment plans, and new patient information. A DVH model is generated from the knowledge-based information in Step S202, and the DVH model is trained in Step S203. The trained model is applied to the new patient data to generate DVH estimates in Step S204.

As previously indicated, the model trainer 326 can use various available methodologies to train the DVH estimation models, such as, but not limited to, parametrization of the structure set and dose matrices for the existing treatment plans. The parametrization can identify and analyze, among other things, the current dose volume histogram curve (i.e., the current/actual DVH line).

Although the model generation and training steps S202 and S203 are illustrated in FIG. 6, it is to be understood that these steps can be separately performed prior to the optimizing, and the resulting trained DVH estimation model saved in the storage medium 323, for example, to be directly used during optimization as the knowledge-based information inputted from source 2.

Figure 8:
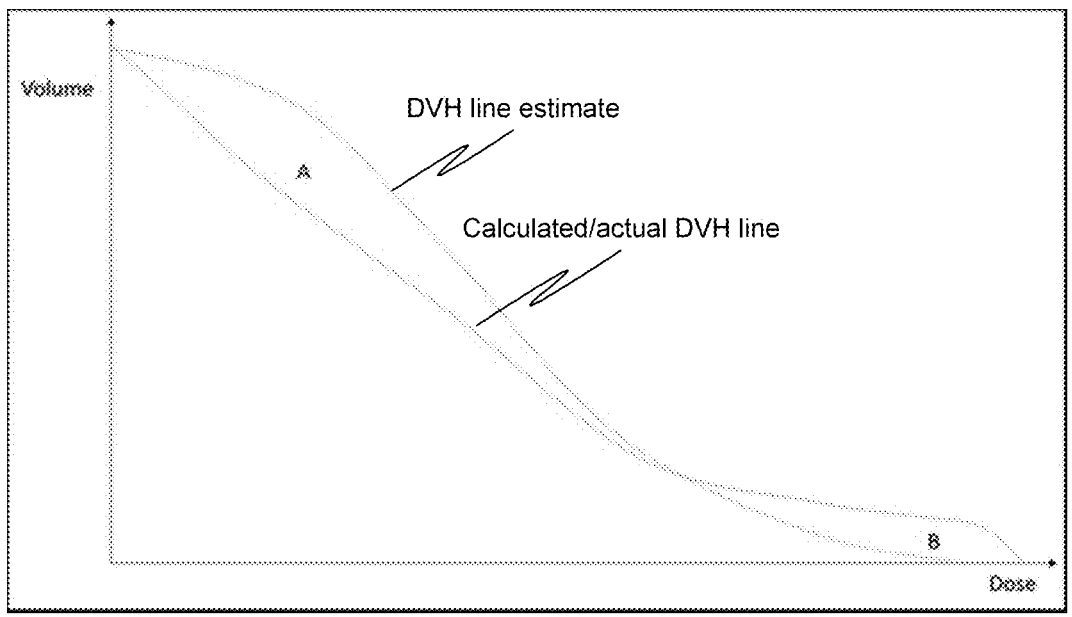
FIG. 8 is an illustration of actual and DVH estimate lines used to convert DVH estimates into clinical goals, according to various embodiments of the disclosed subject matter.

Once the trained DVH model is applied to the new patient, the DVH estimates for each relevant structure of the patient can be obtained in Step S204 in the form of a pair of Dose Volume Histograms (DVHs) representing the lower and upper bounds of the 95% confidence interval of the prediction. Then, for each structure, a DVH line estimate representing the mean between the upper and lower bounds of the DVH estimates can be obtained. FIG. 8 illustrates an exemplary DVH line estimate and an actual DVH line for a structure.

In Step S205, for each structure, the DVH line estimate is compared with the actual DVH line by the DVH converter 331, and the differences are calculated along the entire DVH line estimate (as opposed to calculating differences between the two DVH lines only at specific dose-volume points). The calculated differences can then be used to define a "goal", such as that the actual dose (actual DVH) at a given volume be lower than the estimate dose (i.e., estimate DVH). A "goal" for this type is achieved (i.e., "passes") and has a high quality value when the actual dose at a given volume is lower than the estimate dose.

For example, in area A of FIG. 8 (which is the area defined by the two DVH lines), the actual DVH line is doing better than the estimate DVH line, since the actual dose at any given volume (V) in area A is lower than the estimate dose, whereas, in area B, the actual DVH line is doing worse than the estimate DVH line, since the actual dose at any given volume (V) in this area is higher than the estimate dose. Thus, in area A, the goal is achieved, whereas, in area B the goal is not achieved.

By converting the DVH estimates for each of the relevant structures of the patient into corresponding "goals", a set of "converted clinical goals" are generated in Step S205, to be added to the set of prioritized clinical goals received in Step S206.

Additionally, or alternatively, a priority can be associated with each of the converted clinical goals. For example, a goal generated by converting the DVH line estimate for a target structure could have the same priority as the priority assigned for that structure in the prioritized set of clinical goals (CG). As such, a set of prioritized converted clinical goals can be obtained in Step S205.

Figure 7A:
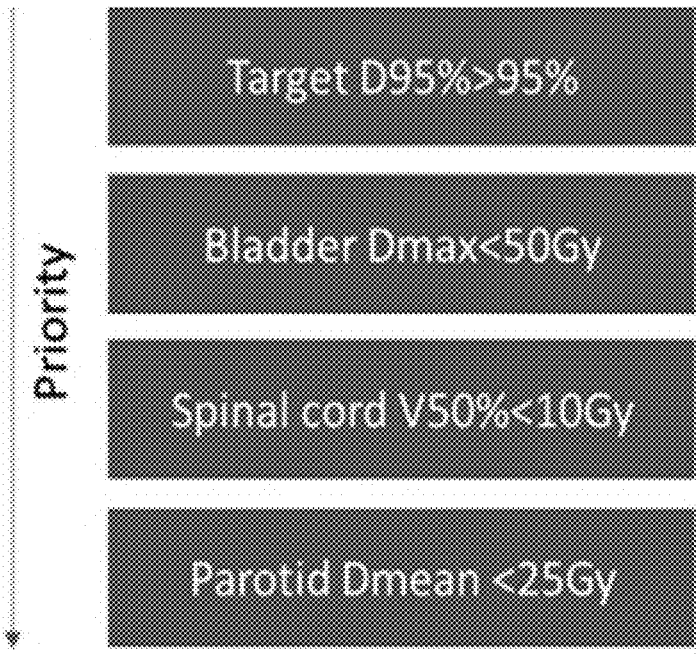
FIG. 7A is an illustration of a set of prioritized clinical goals and associated priorities, according to various embodiments of the disclosed subject matter.
Figure 9:
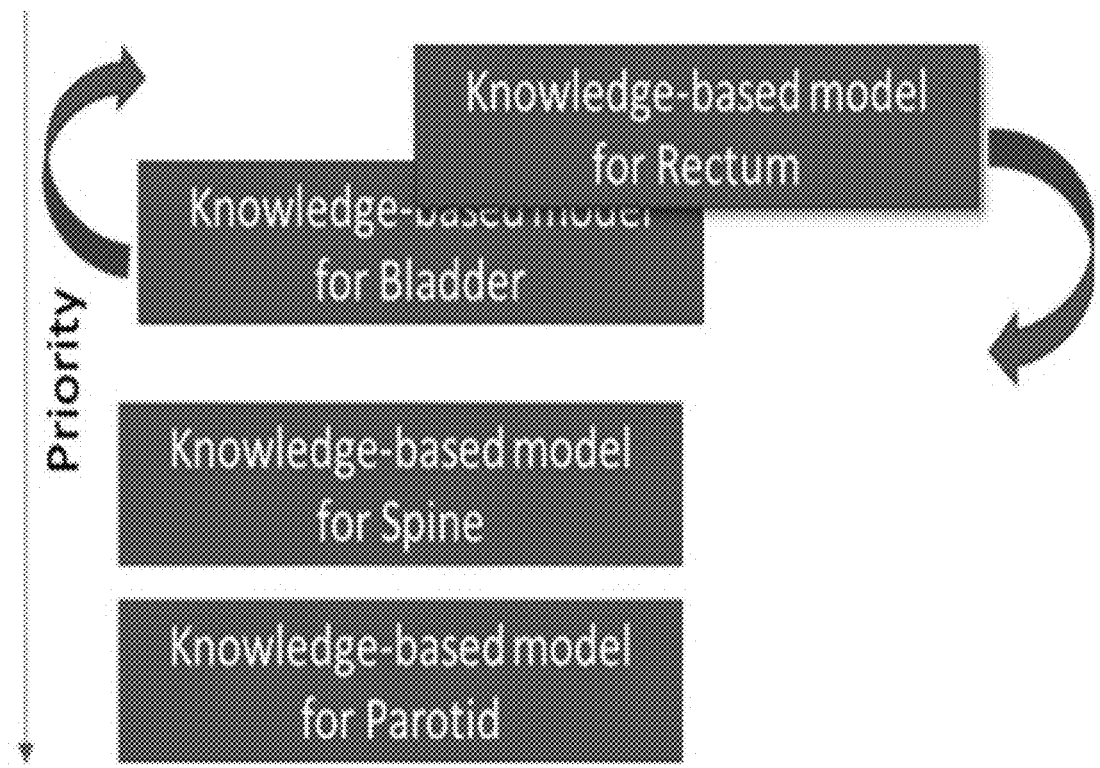
FIG. 9 is an illustration of user-enabled dynamic reorganization of converted clinical goals.

For example, as shown in FIG. 7A, for four prioritized clinical goals (CG) received in Step S206 from a first source:
Goal 1: Rectum (Target) D95%>95%: priority 1
Goal 2: Bladder $D_{max}$<50 Gy: priority 2
Goal 3: Spinal Cord V50%<10 Gy: priority 3
Goal 4: Parotid $D_{mean}$<25 Gy: priority 4,
four "goals" as shown in FIG. 9 can also be generated in Step S205 from the DVH line estimates of the corresponding structures, namely, the target rectum, the bladder, the spinal cord, and the parotid, including the same priorities as the priorities for the clinical goals CG. Thus, the set of prioritized converted goals from Step S205 could include a goal for the rectum DVH line having priority 1; a goal for the bladder DVH line having priority 2; a goal for the spinal cord DVH line having a priority 3; and a goal for the parotid DVH line having a priority 4, for example.

Additionally, or alternatively, the goals can be generated from the DVH line estimate plus one standard deviation instead of the DVH line estimates.

In order to generate treatment plans based on the original set of clinical goals (CG) and the set of converted clinical goals, both sets of goals can be added to the quality metric generator 321 to generate quality metrics $Q_i$ or continuous quality metrics (CQM) in Step S207 that take into consideration the prioritized clinical goals received from the first source, as well as the prioritized converted goals generated from the DVH estimate lines.

A total plan quality, which is a function of the individual quality metric dependent plan qualities can be obtained in Step S208. For the prioritized clinical goals (CG), the prioritization metric values may be considered as the plan quality values. For each of the converted clinical goals, however, a plan quality value can be obtained by summing the negative differences (i.e., the unwanted areas such as area B) over the corresponding DVH line. Each of these plan quality values represents how far away one is from a desired quality for a goal.

The plan quality/CQM function generated in Step S208 will then be a function of the individual quality metric dependent plan qualities, and thus the total plan quality will be a function of the plan quality values of the prioritized clinical goals (CGs) as well as the plan quality values of the goals converted from the DVH estimates.

The total plan quality may represent the cost function. This cost function mathematically represents the dose objectives for a preferred dose-distribution based on both the original set of clinical goals and the generated set of converted clinical goals.

Figure 7B:
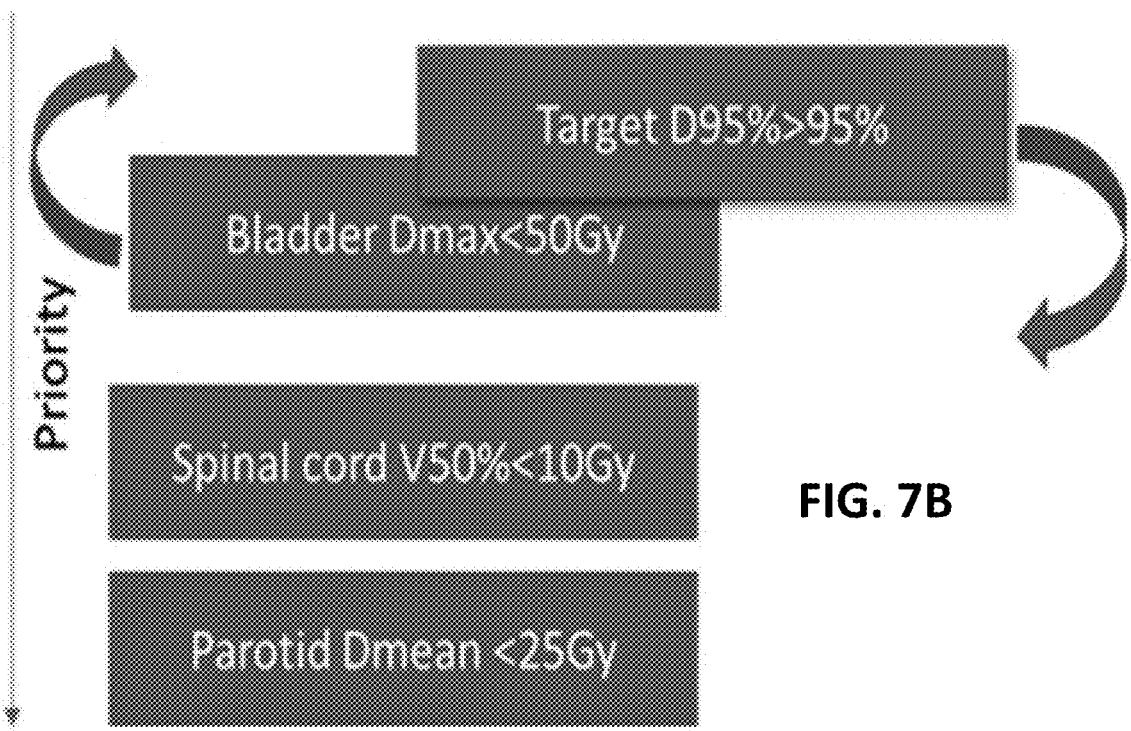
FIG. 7B is an illustration of the user-enabled dynamic reorganization of the clinical goals of FIG. 7A.

By using a plan quality metric that takes into account the prioritized list of clinical and converted goals as an input to the optimization process, both the clinical goal list and the converted goal list can be dynamically re-ordered by the user in order to explore the dose distributions from other priorities, as illustrated in FIGS. 7B and 9.

Alternatively, or additionally, each of the goals obtained by converting a corresponding DVH line estimate, can be used to set "virtual" stretch goals in the prioritized clinical goal CG metrics. For example, if there is a clinical goal CG in the list of prioritized clinical goals that wants less than 40 Gy for less than 20% of volume in the parotid having priority 3, and the DVH estimation model shows that the actual DVH in a population of plans for 20% volume is 35 Gy, a "virtual stretch goal" having a lower priority (i.e., priority 4, for example) can be formulated based on the DVH estimate. Such a virtual stretch goal could be, for example, to require 35 Gy for less than 20% of volume in the Parotid. This virtual stretch goal could be added to the original list of prioritized clinical goals. This way, the optimizer 329 in Step S209 will try to achieve the stretch goal after it has achieved the original goal.

Alternatively, or additionally, the DVH estimates can be used to obtain information about the stretch goals, meaning that they are not converted into actual clinical goals with priority, dose and volume values, but rather they give information to the clinical goal optimizer 329 regarding how far beyond the actual goals can the dose be pushed.

Alternatively, or additionally, a whole set of prioritized clinical goals can be generated by converting corresponding DVH line estimates into goals. In such a case, the set of converted prioritized clinical goals, instead of the original set of prioritized clinical goals, can be used in the optimization and the evaluation process.

Generating Helping Objectives

When optimizing a treatment plan using a set of prioritized clinical goals as an input metric, the dose distribution that fulfills the goals can still be clinically unacceptable. This is due to missing information in many clinical goal templates that are widely used. In a standard, non-automatic workflow, this problem is bypassed by manually adding dose-volume objectives that shape the optimized dose distribution while fulfilling the original clinical goal metrics. This, however, can be laborious work that includes many trials and errors, and therefore cannot be used in automatic planning.

In order to solve this problem, in an automatic treatment planning process such as described herein, a method is employed to automatically derive helping objectives from the set of clinical goals, in order to guide the automatic clinical goal-based dose optimization to output clinically acceptable plans.

Figure 10:
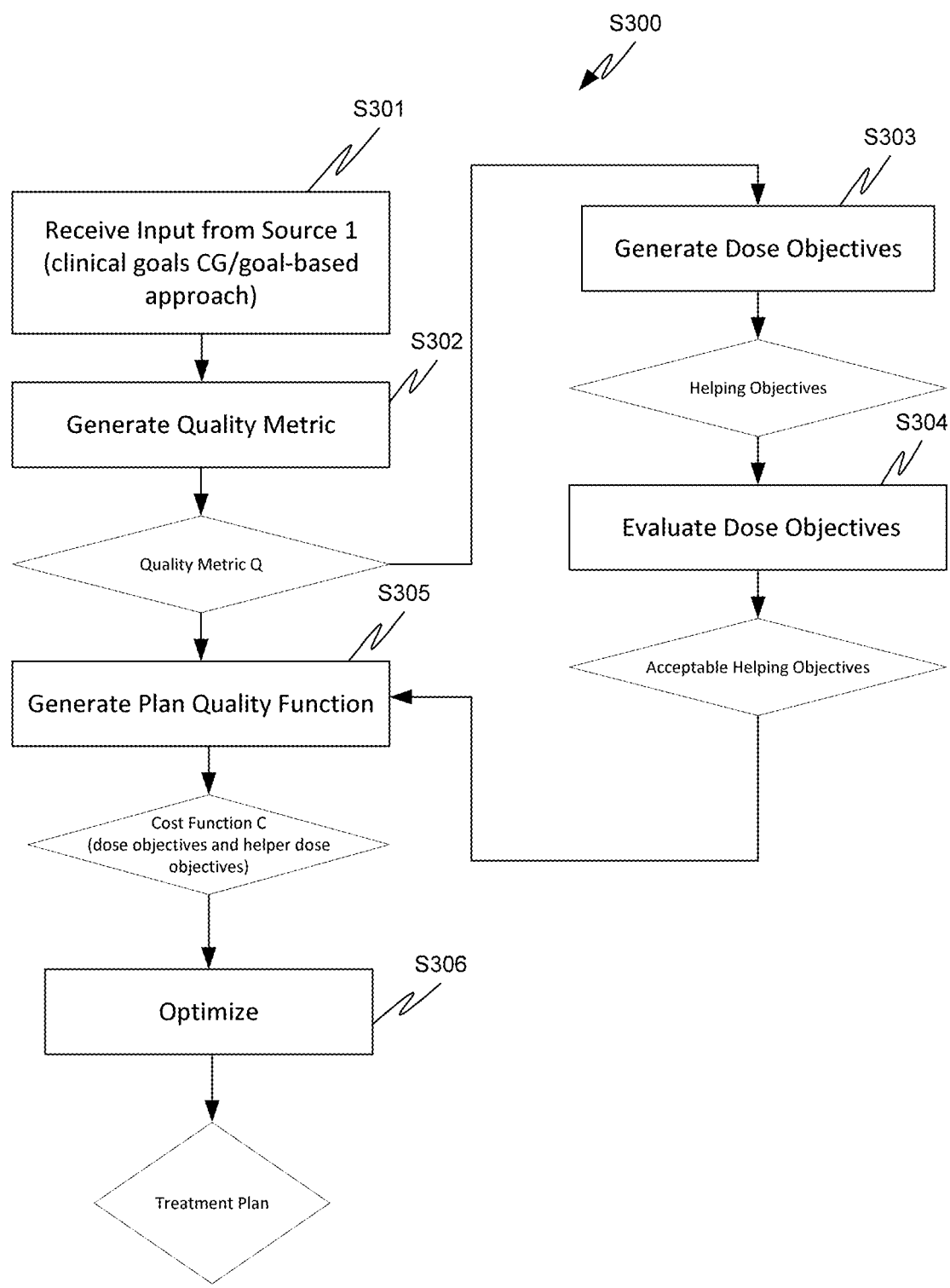
FIG. 10 is a process flow diagram for automatic helper objective generation, according to various embodiments of the disclosed subject matter.

A process S300 for deriving such helping objectives and for generating acceptable treatment plans using the helping objectives is shown in FIG. 10. In Step S301, a set of clinical goals are received via the user interface 311. In the case in which one or more of the received clinical goals do not contain sufficient information to describe the desired dose coverage, helping objectives are automatically generated by the dose objective generator 327 in Step S303 to shape the DVH curve representing the dose coverage fulfilling the original clinical goal metrics to include the dose coverage that is missing from the input metric. The helping objectives are thus additional dose objectives that are automatically added/placed at different dose volume positions of the DVH curve to shape the dose distribution while still fulfilling the original clinical goal metrics.

In order to automatically generate the helping objectives, the algorithm is configured to make one or more assumptions, such as:
1) The user wants the clinical goals to be met comfortably (i.e., with a margin); and that
2) The user wants uniform dose to the target and low dose outside the target if the geometry of the patient allows it, for example.

These assumptions are exemplary only, and any other applicable assumptions may be made.

Based on these assumptions, the optimization algorithm automatically adds helping objectives to shape the dose in the vicinity of the structure volume depending on the:
a) Dose prescription;
b) Type of structure;
c) Common knowledge as to what is clinically viable; and
d) How robust the dose needs to be for any disturbance, such as post-processing or dose scaling.
  The helping objectives for target goals can follow the following rules:
1. A main helper objective is added at a tighter dose-volume point to the goal. For example, for a goal having a priority 1, the helping objective could be added at D96%>46 Gy.
2. If the goal is a lower goal (<), a helping objective could be added at 100% volume (i.e., $D_{min}$), and if the goal is an upper goal (>), a helping objective can be added at 0% volume (i.e., $D_{max}$). The dose points for these min/max helping objectives can be determined heuristically, such as requiring the helping objectives to be within +/−10% of the original goal value.
3. Additional helping objectives could be added between the min/max helping objectives and the main helping objective. The additional helping objectives could be, optionally, equally spaced in the volume axis.

The helping objectives obtained in Step S303 can also be evaluated in Step S304, and the acceptable helping objectives are added to the dose objectives of the original clinical goals CG to generate a cost function in Step S305 that, when optimized in Step S306, gives a clinically acceptable treatment plan. Thus, the dose objectives together with the helping objectives guide the automatic clinical goal-based dose optimization to output clinically acceptable plans.

In an embodiment, the helping objectives generated in S303 are dose objectives added at dose/volume positions that are above and below an exponential curvature following the volume value given by the DVH curve of the original clinical goals. Such helping objectives help define a "shoulder" and "tail" of the DVH curve.

Figure 11A:
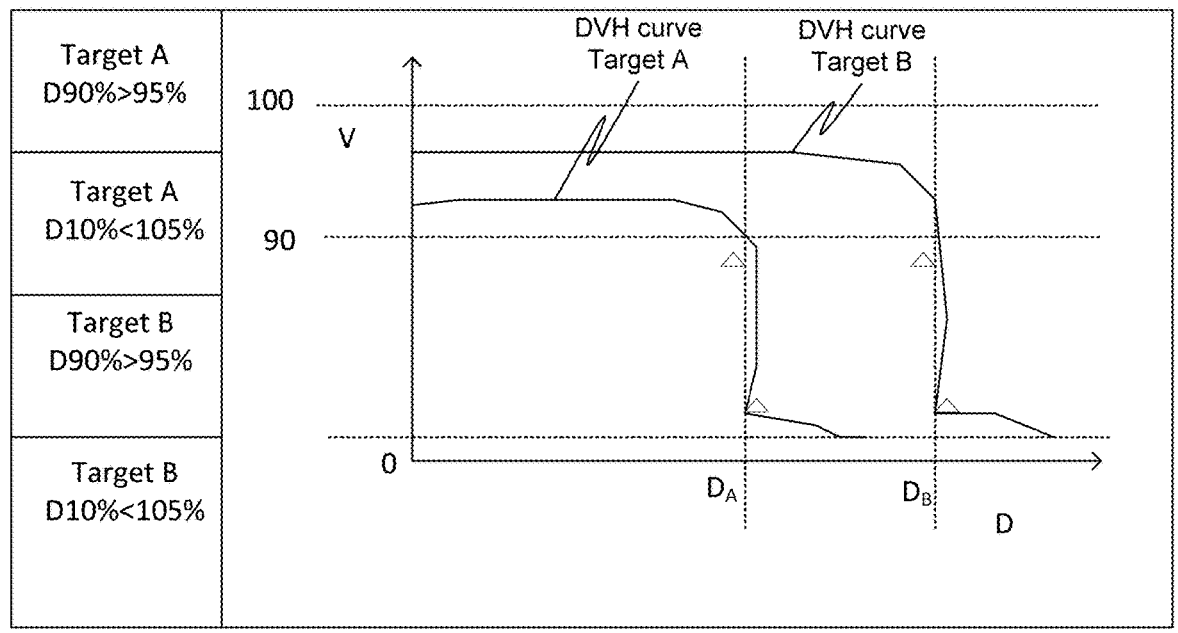
FIG. 11A is an illustration of dose curves obtained for two target structures based clinical goals missing information.
Figure 11B:
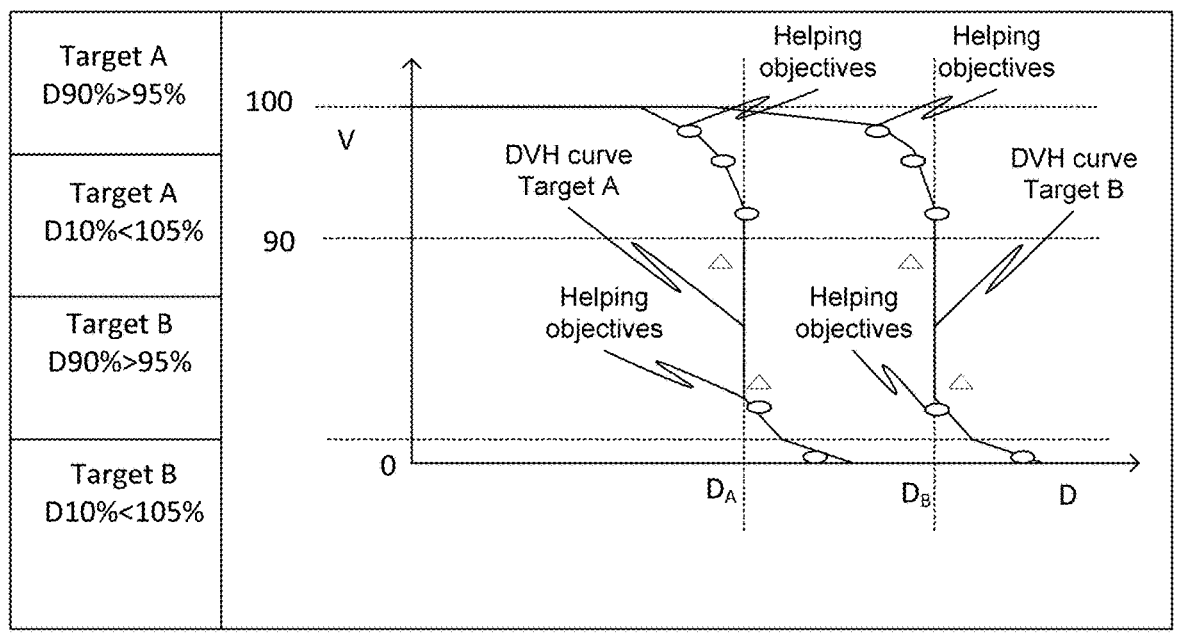
FIG. 11B is an illustration of dose curves obtained for the two target structures of FIG. 11A using helper objectives.

An example of such helping objectives is shown in FIGS. 11A and 11B. FIG. 11A shows the dose distributions (DVH curves) for two structures, structure A and structure B, representing the dose coverage fulfilling the following clinical goals:
1. Goal 1: Target A D90%>95%
2. Goal 2: Target A D10%<105%
3. Goal 3: Target B D90%>95%
4. Goal 4: Target B D10%<105%

Each of the targets A and B are defined by two target volume values, shown as the triangles in FIG. 11A and FIG. 11B, one that wants the DVH curve to pass above it, and one that wants to DVH curve to pass under it. Although the dose distribution obtained for these clinical goals gives information regarding the dose in the 10%-95% volume range, there is no information provided for the volume range above 90% and under 10%. Thus, the clinical goals Goal 1 through Goal 4, do not provide sufficient information to control this volume range. Optimizing a cost function based only on these clinical goals may provide a clinically unacceptable treatment plan due to unacceptably low minimum dose or unacceptably high maximum dose.

Adding helping objectives (shown as circles in FIG. 11B) at dose/volume positions that are above and below the exponential curvature following the two target volume values (i.e., the set of triangles) for each of the two structures A and B, as shown in FIG. 11B, helps define the shoulder (i.e., volume range above 95%) and tail (i.e., volume range below 10%) of the DVH curves. The resulting DVH curves are now fully controlled in the whole range of 0-100% of the volume range, and the resulting treatment plan is clinically acceptable.

Additionally, or optionally, the dose axis positions of the helping objectives can be further offset to account for scaling errors.

Additionally, or optionally, helping objectives that control the dose values outside a target structure can also be generated, so as to restrict dose values that are too high outside of the target structure.

As indicated above, the helping objectives obtained in Step S303 are optionally evaluated in Step S304. This evaluation can include evaluating each generated helping objective for conflicts between it and the dose objectives of the original clinical goal set. For example, each helping objective may be evaluated between what it wants and what the dose objectives of the original clinical goals want. So, if there are two geometrically overlapping structures, a situation where the dose objectives are in conflict in the overlapping volume should be avoided. Therefore, helping objectives that would create such overlap, would be deemed unacceptable.

Additionally, or optionally, additional objectives for the missing information from the clinical goals may be further manually or automatically added.

Resolving Conflict Between Clinical Goals

Automated treatment planning strives to achieve the clinical goals given by the physician as well as possible. However, checking for the physical feasibility of given clinical goals is tedious. For an automated planning system to be clinically useful, physicians using the system can't be required to perfectly check the physical feasibility of the goals they are asking from the automated planning system. This results in some of the physician supplied clinical goals to be conflicting with each other. In other words, all of the goals cannot be achieved simultaneously. Conflicts in clinical goals cause problems for the automated planning system for which the clinical goals have a well-defined priority order.

To solve problems arising from conflicting clinical goals, an optimization method is devised that automatically modifies the clinical goals to make them achievable.

Generally, when the optimizer 329 receives the clinical goals (CGs) that have been prioritized by the user/physician, optimization starts by working on the highest priority goal by optimizing the fluences to make that goal pass. Once the highest priority goal has been achieved, optimization moves on to the next clinical goal in the priority list. This process continues through the whole list of clinical goals.

When optimization encounters a clinical goal that may be conflicting or is incompatible with another goal in the list, the optimization adapts and replaces the incompatible goal with a compatible one. A compatible goal is one which allows all of the higher priority goals to pass, while providing an as-good-as-possible achieved value for the original lower priority incompatible goal. With the replacement of the incompatible goal, the optimization can continue the treatment plan optimization through rest of the goals in the list.

Figure 12:
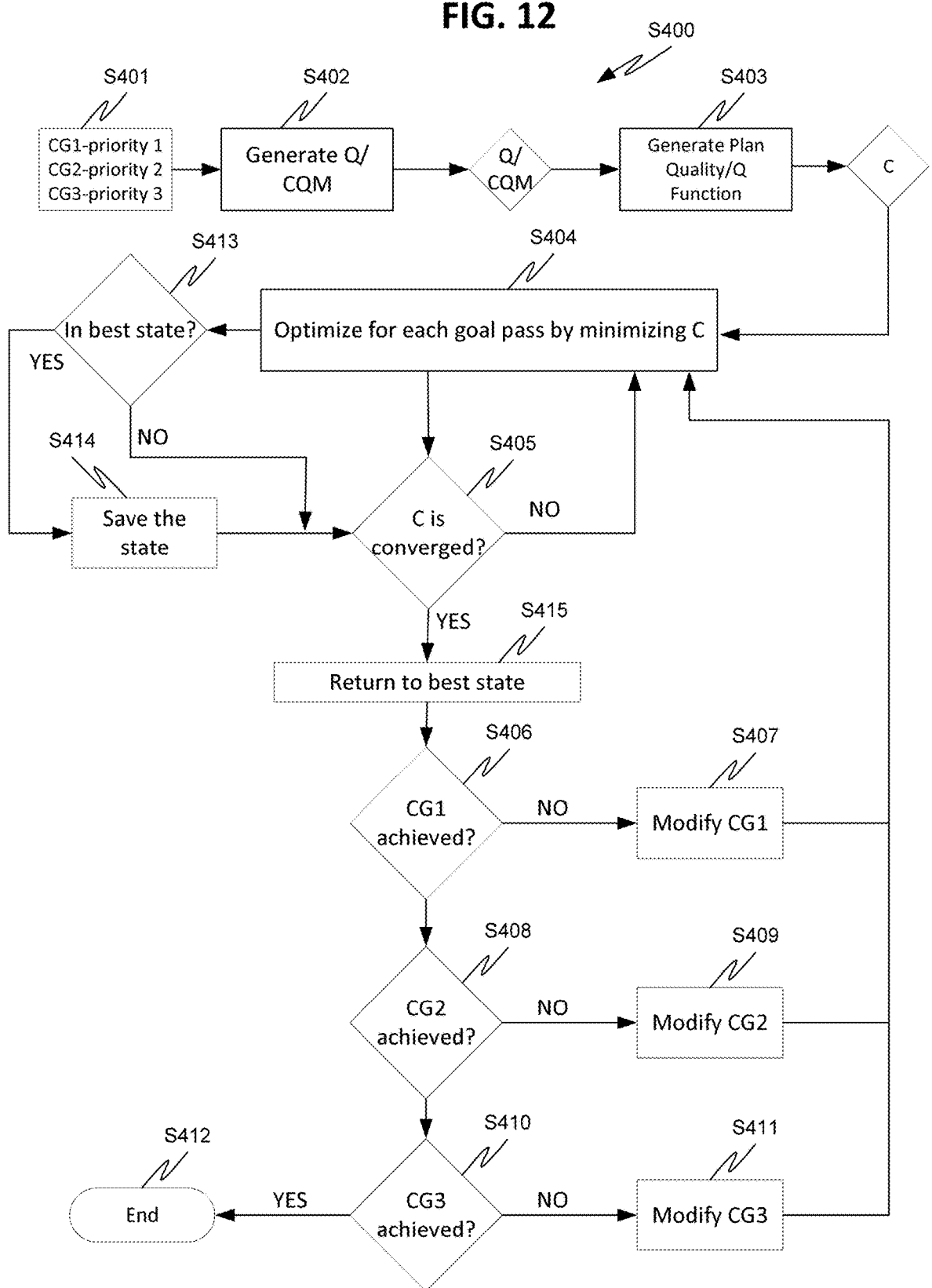
FIG. 12 is a process flow diagram for automatic adjustment of incompatible clinical goals.
Figure 13:
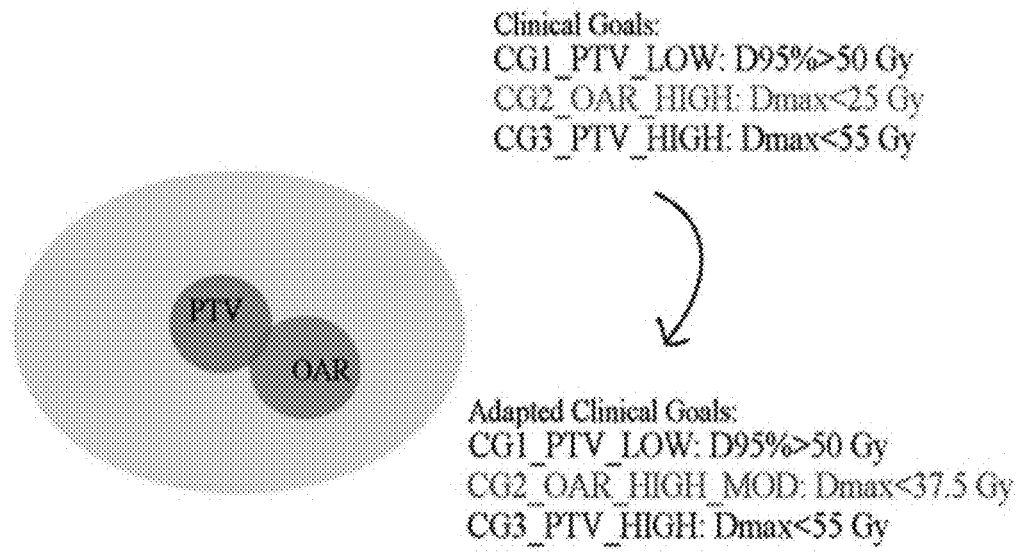
FIG. 13 is an illustration of clinical goals and adapted clinical goals obtained in the process of FIG. 12.

A process S400 that implements such an automatic adaptation of the optimization process is illustrated in FIG. 12. In Step S401, a set of prioritized clinical goals is received. The set includes, for example, three clinical goals CG1, CG2, and CG3, with corresponding priorities 1, 2, and 3, for a case involving two structures, a planning target volume (PTV), and an organ at risk (OAR), as shown in FIG. 13:

Goal 1 (CG1): D95%>50 Gy (Dose received by 95% of the PTV volume is at least 50 Gy): priority 1;
Goal 2 (CG2): Dmax<25 Gy (The maximum dose received by the OAR is below 25 Gy): priority 2:
Goal 3 (CG3): Dmax<55 Gy (The maximum dose received at PTV is below 55 Gy): priority 3.

In Step S402, quality metrics Qi or continuous quality metrics (CQM) may be generated for the prioritized set of clinical goals, based on which one or more plan quality functions can be generated in Step S403. Then, during optimization in Step S404, the optimizer 329 will try to optimize fluences to make each of the clinical goals CG1, CG2 and CG3 pass, by minimizing the cost function (C) generated based on the plan quality functions. To minimize the cost function (C), the optimization algorithm attempts to find a local or global minima of the cost function (C), which is the point where further tweaks of the function parameters produce little or no changes in the loss. Convergence to this minimum is a gradual process which can be achieved through one or more optimization iterations. As the optimization model iterates, the parameters of the cost function (C) are tweaked or corrected to further reduce the cost function, and so as to gradually have the cost function (C) converge towards this minimum in S405.

To optimize for each goal, the optimization process begins in S406 by creating fluences that attempt to satisfy the highest priority goal CG1. If CG1 is not achieved, the optimization algorithm automatically modifies CG1 in S407. The number of iterations that the optimization model may go through before deciding to modify CG1 may be a previously predetermined number.

Alternatively, or additionally, the number of iterations that the optimization model can go through before deciding to modify CG1 may be a number that has been previously set by a user.

Alternatively, or additionally, the decision as to when to stop trying to achieve CG1 and proceed with modifying CG1 can be adaptively made based on results obtained in previous iterations.

Alternatively, or additionally, the decision as to when to stop trying to achieve CG1 and proceed with modifying CG1 can be made based on a predetermined length of trying time.

Alternatively, or additionally, the decision as to when to stop trying to achieve CG1 and proceed with modifying CG1 can be made based on the minimization process applied.

Alternatively, or additionally, the decision as to when to stop trying to achieve CG1 and proceed with modifying CG1 can be made based on a combination of time lapsed and minimization approach used.

Alternatively, or additionally, any other suitable approaches to automatically decide when to modify CG1 can be implemented.

While trying to meet goal CG1, the optimization gathers information on the values it has been able to achieve for goal CG1. In other words, the optimizer knows which minimum dose values are at least achievable for CG1. From these known achievable values, the optimizer will pick a modified goal value for CG1 in S407 (i.e., MOD CG1) which is as close to the given goal value for CG1 as possible.

For example, if it is determined that the best result the optimizer was able to obtain fluences for was 45 Gy for CG1, this value will replace the original CG1 value of 50 Gy. The new adapted value for CG1, namely MOD CG1, becomes D95%>45 Gy. This way the optimization adapts to the incompatible goal CG1 by replacing it with a compatible goal MOD CG1. With this replacement, the optimization can find a state where MOD CG1 passes and can start optimizing the next goal in the list, namely CG2 in Step S408, while making sure that CG1, if it hasn't been modified, or MOD CG1, if CG1 has been modified, remains passing.

Alternatively, or additionally, instead of replacing the original CG1 value with a modified MOD CG1 value, it could be implemented that the original goal CG1 be replaced with a first goal having the MOD CG1 value and a second stretch goal having a lower priority and having a value that is between the MOD CG1 value and the original CG1 value.

It is to be understood that any manner of goal value modification for CG1 that improves results may be implemented.

Once CG1 or MOD CG1 is achieved, optimization moves to the next goal in the priority list, namely CG2. If it is determined in Step S408 that CG2 has a conflict with CG1, if CG1 hasn't been modified in S406, or with MOD CG1, if CG1 has been modified in S407, such that CG2 can't pass while CG1 or MOD CG1 is passing (i.e., CG2 can't be achieved if CG1 or MOD CG1 is achieved), it modifies CG2 in S409 to allow for both the CG1 or MOD CG1 and the modified MOD CG2 of S409 to pass.

Initially, the optimization is not aware of the incompatibility between CG1 or MOD CG1 and CG2 and tries to achieve CG2. After some time of trying to unsuccessfully meet CG2, it concludes that goal CG2 is not compatible with CG1 or MOD CG1. At this point the modified goal MOD CG2 of S409 is used. The number of iterations that the optimization model may go through before deciding to modify CG2 may be a previously predetermined number.

Alternatively, or additionally, the number of iterations that the optimization model may go through before deciding to modify CG2 can be a number that has been previously set by a user.

Alternatively, or additionally, the decision as to when to stop trying to achieve CG2 and proceed with modifying CG2 can be adaptively made based on results obtained in previous iterations.

Alternatively, or additionally, the decision as to when to stop trying to achieve CG2 and proceed with modifying CG2 can be made based on a predetermined length of trying time.

Alternatively, or additionally, the decision as to when to stop trying to achieve CG2 and proceed with modifying CG2 can be made based on the minimization process applied.

Alternatively, or additionally, the decision as to when to stop trying to achieve CG2 and proceed with modifying CG2 can be made based on a combination of time lapsed and minimization approach used.

Alternatively, or additionally, any other suitable approaches to automatically decide when to modify CG2 may be implemented.

While trying to meet the incompatible goal CG2, the optimization gathers information on the values it has been able to achieve for goal CG2 while the higher priority goal CG1 or MOD CG1 is passing. In other words, the optimizer knows which maximum dose values are at least achievable for CG2. From these known achievable values, the optimizer will pick a modified goal value for CG2 in S409 (i.e., MOD CG2) which is as close to the given goal value for CG2 as possible, while still respecting the higher priority goal CG1 or MOD CG1.

For example, if it is determined that the best result the optimizer was able to obtain fluences for was 37.5 Gy for CG2, this value will replace the original CG2 value of 25 Gy. The new adapted value for CG2, namely MOD CG2, becomes Dmax<37.5 Gy. This way the optimization adapts to the incompatible goal CG2 by replacing it with a compatible goal MOD CG2. With this replacement, the optimization can find a state where both the CG1 or MOD CG1 and the MOD CG2 pass, and can start optimizing the next goal in the list, namely CG3 in Step S410, while making sure that both CG1 or MOD CG1 and MOD CG2 remain passing.

Alternatively, or additionally, instead of replacing the original CG2 value with a modified MOD CG2 value, it could be implemented that the original goal CG2 be replaced with a first goal having the MOD CG2 value and a second stretch goal having a lower priority and having a value that is between the MOD CG2 value and the original CG2 value.

It is to be understood that any manner of goal value modification for CG2 that improves results may be implemented.

The optimization will again try to create fluences that satisfy CG3 as well as all of the higher priority goals, namely CG1 or MOD CG1 and CG2, if CG2 has not been modified in S408, or MOD CG2, if CG2 has been modified in S409. After some time of trying to unsuccessfully meet goal CG3, it either concludes in S410 that CG3 is not compatible with CG1 or MOD CG1, and/or with CG2 or MOD CG2. If it concludes in S410 that it is not compatible with CG1 or MOD CG1, or with CG2 or MOD CG2, it modifies CG3 in S411 to MOD CG3. The number of iterations that the optimization model may go through before deciding to modify CG3 may be a previously predetermined number.

Alternatively, or additionally, the number of iterations that the optimization model may go through before deciding to modify CG3 can be a number that has been previously set by a user.

Alternatively, or additionally, the decision as to when to stop trying to achieve CG3 and proceed with modifying CG3 can be adaptively made based on results obtained in previous iterations.

Alternatively, or additionally, the decision as to when to stop trying to achieve CG3 and proceed with modifying CG3 can be made based on a predetermined length of trying time.

Alternatively, or additionally, the decision as to when to stop trying to achieve CG3 and proceed with modifying CG3 can be made based on the minimization process applied.

Alternatively, or additionally, the decision as to when to stop trying to achieve CG3 and proceed with modifying CG3 can be made based on a combination of time lapsed and minimization approach used.

Alternatively, or additionally, any other suitable approaches to automatically decide when to modify CG3 can be implemented.

As before, while trying to meet the incompatible goal CG3, the optimization gathers information on the values it has been able to achieve for the goal CG3 while the higher priority goals CG1 or MOD CG1 and CG2 or MOD CG2 are passing. In other words, the optimizer knows which maximum dose values are at least achievable for CG3. From these known achievable values, the optimizer will pick a modified goal value for CG3 in S411 (i.e., MOD CG3), which is as close to the given goal value for CG3 as possible, while still respecting the higher priority goals CG1 or MOD CG1 and CG2 or MOD CG2.

Alternatively, or additionally, instead of replacing the original CG3 value with a modified MOD CG3 value, it could be implemented that the original goal CG3 be replaced with a first goal having the MOD CG3 value and a second stretch goal having a lower priority and having a value that is between the MOD CG3 value and the original CG3 value.

It is to be understood that any manner of goal value modification for CG3 that improves results may be implemented.

The process S400 ends at S412 when fluences are found that pass all of the goals in the list.

Additionally, or optionally, the process S400 can also include a Step S413 of determining at each iteration whether the current state is the best state, and a Step S414 of storing the best optimization state (fluences, objectives and their weights, etc.) during the optimization. This state corresponds to the one where all higher priority goals are passing and the goal which the optimization is working on currently is in the best state it has been. When the optimization concludes that the goal it is currently working on is incompatible with other goals, it can easily return to the best state in Step S415. This state therefore can automatically be set to be the state which will be used to determine the value for the adapted clinical goal, and the optimization can then continue from this state with all the goals passing from the highest priority one to the next goal in the list.

Additionally, or optionally, the process S400 can also include storing the adapted CG values for use at a later stage in the optimization process.

It is to be understood that the number of clinical goals and the values for each original and modified clinical goal used in process S400 are exemplary only, and that the automatic adaptation process of S400 can be applied to any number of clinical goals and any suitable modified values.

It is also to be understood that the timing of automatic modification of the clinical goals described herein are exemplary only and that any other suitable manner of goal modification can be implemented.

Process S400 can also be applied to an embodiment where the clinical goals are represented as continuous quality metrics (CQM), in which case, when an unachievable goal is encountered, the continuous quality metric (CQM) for that goal can be set to an already achieved (CQM) level for all priority levels higher and equal to the current level. Thus, when the clinical goals are modified as in the process S400, the corresponding continuous functions $G_i$ representing the (CQMs) (i.e., Q-functions), and which define the different plan qualities (i.e., describe the importance of obtaining a certain achieved value for the Q metric for a given priority level P), can also be modified.

Figure 14A:
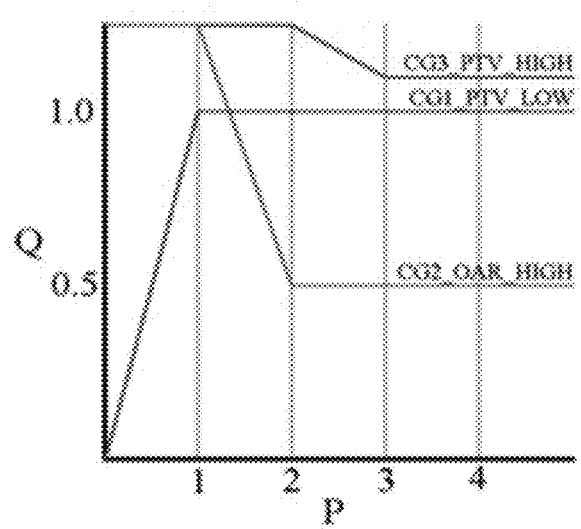
FIG. 14A is a chart depicting continuous quality metric functions for clinical goals that are dose goals, according to various embodiments of the disclosed subject matter.
Figure 14B:
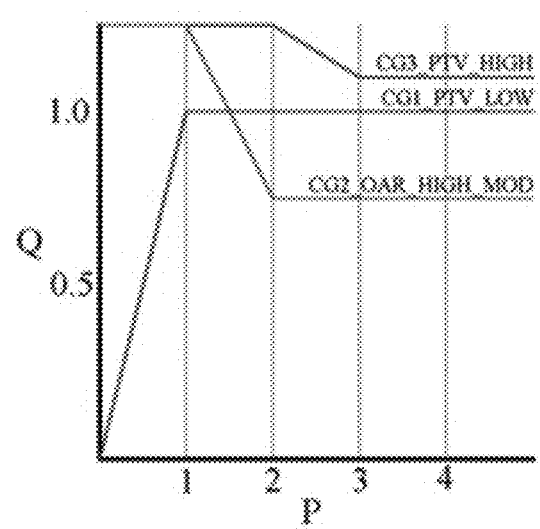
FIG. 14B is a chart depicting continuous quality metric functions for clinical goals after manipulation of a conflicting goal, according to various embodiments of the disclosed subject matter.

For example, FIG. 14A shows the Q-functions for the original clinical goals CG1, CG2 and CG3, and FIG. 14B illustrates the Q-functions for the modified clinical goals CG1, CG2, CG3 of process S400. The Q values on the Y-axis correspond to the portions of the prescription dose. For example, Q=0 corresponds to dose of 0 Gy, Q=0.5 corresponds to a dose of 25 Gy, and Q=1 corresponds to a dose of 50 Gy. The P values on the X-axis correspond to the priority levels of each of the goals (i.e., P=1 means priority 1, P=2 means priority 2, etc.).

As shown in FIG. 14A, the original Q metric required that CG1 is to achieve the Q-value of 1, and thus a dose of 50 Gy, at the P value 1, and thus at priority 1. CG2 is to achieve the Q-value of 0.5, and thus a dose of 25 Gy, at the P value of 2, and thus at priority 2. CG3 is to achieve a Q-value of 1.1, and thus a dose of 55 Gy, at the P value of 3, and thus at priority 3.

As shown in FIG. 14B, on the other hand, the modified Q metric requires that CG1 is to achieve the Q-value of 1, and thus a dose of 50 Gy, at the P value 1, and thus at priority 1. CG2 is to achieve the Q-value of 0.75, and thus a modified dose of 37.5 Gy, at the P value of 2, and thus at priority 2, and CG3 is to achieve a Q-value of 1.1, and thus a dose of 55 Gy, at the P value of 3, and thus at priority 3.

As such, regardless of whether the clinical goals are represented as quality metrics Q or as continuous quality metrics (CQM), the optimizer is configured to automatically modify the user defined prioritized clinical goals during a conflict by automatically modifying a lower priority goal until all higher priority goals in the set are satisfied.

Automatic Plan Optimization in Adaptive Therapy

Adaptive radiation therapy is a process by which, using subsequent images, an original treatment plan can be adjusted to counteract the anatomical changes that occur in the patient. The adaptive radiation therapy process, as shown in FIG. 2, is a closed-loop radiation treatment process where the treatment plan can be modified (adapted) using a systematic feedback of measurements. By systematically monitoring treatment variations and by incorporating them to re-optimize the treatment plan during the course of treatment, the adaptive radiation therapy improves radiation treatment.

Adaptive radiation therapy can occur at three different timescales, namely, off-line between treatment fractions, on-line immediately prior to a treatment fraction, and in real-time during a treatment fraction.

In an off-line adaptive therapy process, during each treatment fraction, a new image (CT or CTBC image, for example) of the patient is acquired before or after each of the fractions and the images are evaluated to determine multi-day locations of the target volumes. Based on this, a new plan (i.e., scheduled plan, for example) can be developed to better reflect the range of motion of the target volumes.

In an on-line adaptive therapy process, the radiation therapy system can be used prior to a fraction to validate or adjust the patient treatment plan for the treatment delivery. The imaging system can thus be used to concurrently modify the treatment delivery to reflect the changes in the patient's anatomy.

In a real-time (on-couch) adaptive therapy process, the radiation therapy system can be used during a treatment fraction. On-couch adaptive radiation therapy allows adjustment of treatment plan based on tumor and anatomical changes while the patient is on the treatment table.

In an adaptive workflow shown in FIGS. 2, and 15-18, for each treatment session, the clinician is offered two plans to choose from for the treatment. The first plan is a scheduled plan, and the second plan is an adapted plan, which is the plan that is adapted for the image of the day, namely, the treatment session image. Both plans are displayed for the clinician, and based on the displayed image data, the clinician makes a decision as to which plan is to be used to treat the patient.

Generating and optimizing an adapted plan in an adaptive workflow is time consuming, however. In order to speed up this process, a method is employed whereby the generation of a new adapted plan does not start from scratch, but instead starts with information contained in the scheduled plan, the amount of information used from the scheduled plan depending on the quality of the scheduled plan.

In an exemplary adaptive workflow shown in FIGS. 2, and 15-18, in order to generate the scheduled and the adapted plans, first the set of adaptive directives developed by the prescriber, are either sent to the controller 200 to be saved therein and/or are made available during the adaptive therapy session via the departmental information system (DICOM, for example). The reference image in the set of directives may be an image that was obtained previously, e.g., in a different imaging session, for the same or a different patient, that may have occurred on a different day, or on the same day.

The reference image may also be an image of a different individual, in which case, image registration can be used to map the patient image to an atlas patient image. The reference image may also be an image that was artificially created via artificial intelligence (AI) segmentation that does not correspond to any individual.

In an exemplary embodiment, the reference image is a planning image obtained for the patient 110 during the treatment planning phase. The reference image can include a set of delineated reference structures, such as one or more target volumes (PTV, CTV, GTV, for example), one or more affected organs (OARs, for example), one or more anatomical structures of interest (body outlines, for example), as well as one or more non-volumetric structures, for example).

Once the set of adaptive directives are made available at the treatment site, the clinician executes the first level of treatment modification, which is setting the patient 110 on the treatment couch 112 the same way as for a standard radiation therapy treatment and moving the patient to the imaging position S502, which essentially means that the patient 110 is taken to the radiation therapy system 100 isocenter, using traditional skin marks indicating the location of the isocenter.

After the patient setup, the next step S503 is to acquire one or more treatment session images of the portion of the patient 110 that is of interest, using the radiation imaging device 101. In an exemplary embodiment, the treatment session image is a 3D or 4D CBCT scan for example obtained during a treatment session by irradiating the region of interest of the patient 110 with radiation 120. This treatment session image may show boney structures of the patient but does not include any delineations of target volumes or other structures.

Then, the user can initialize the generation of contours of the reference structures on the treatment session image to obtain a treatment session patient model in S504. When the treatment session image (i.e., the CBCT image, for example) is acquired in S503, the center of the treatment session image corresponds to the acquisition isocenter. If the patient 110 is treated by aligning the acquisition isocenter with the system isocenter, the patient 110 will not be treated correctly, since, as shown in FIG. 18, the session target volume does not align with the planned target volume. In order to determine the correct treatment isocenter in S505, the system 100 is prompted in S600 to automatically align the planned target volume of the planned patient model obtained to the session target volume of the session patient model obtained in S504.

As shown in FIG. 18, this alignment provides the difference between the acquisition isocenter and the reference treatment isocenter. From this difference, the translation (X, Y, Z) values, namely, by how much in the X, Y, and Z direction does the patient 110 need to be moved for the two isocenters to align, is calculated. The calculated translation values are then applied to the acquisition isocenter so that the treatment isocenter location is determined in S601. This treatment isocenter location is then provided to a dose volume calculation algorithm which, using the information regarding the original treatment plan, generates the scheduled plan in S602.

The scheduled plan can include radiation dosage information and beam shape information (i.e., MLC configuration) for one or more of the control points (CPs) necessary to effect the desired treatment of the patient. The scheduled plan generated in S505 can also be applied to a dose calculation algorithm to calculate in S506 the radiation dose to be applied to the session target volume according to the scheduled plan. The scheduled dose matrix so generated can be sent together with the generated scheduled plan and scheduled isodose values to a display device of system 100 to be displayed for the user in S509.

To generate the adapted plan, in S507, the propagated session structures together with the scheduled plan are used as inputs to an automated plan generation algorithm in S700. The plan generation algorithm can combine several components from existing optimization models (Photon Optimization algorithm (PO-GPU) for VMAT and IMRT, SmartLMC algorithm for leaf sequencing, RapidPlan for DVH-estimation, FTDC-GPU for optimization dose calculation, AcurosXP-GPU for final dose calculation, for example), with an additional component that allows for the automatic generation, automatic selection, and automatic continuous modification of optimization parameters by which the algorithm S700, and ultimately the generated plan, are optimized.

The automated plan generation algorithm of S700 takes the propagated session structures (i.e., target structure, OARs) as input to modify the scheduled plan based on the new anatomy. The treatment parameters of the scheduled plan for one or more control points (CP) can be used in S701 to automatically generate a set of optimization parameters/criteria for the adaptive plan generation.

For example, based on the (MLC) configuration for each control point (CP) in the scheduled plan, the dose distribution for the current plan can be calculated. The calculated dose distribution indicates the actual dose distribution in the target structure and the OARs that can be achieved based on the current plan.

Since a mapping of the priority value P (i.e., priority 1, priority 2, priority 3, etc.) with respect to an original clinical goal (CG) to an achieved value of that goal (i.e., the actual dose achieved for that goal) gives the plan quality for that goal, a plan quality for the current plan with respect to an original clinical goal (CG) can be determined from the calculated dose distribution. This can be done by determining the priority value P corresponding to the actual dose value for that goal. In the case that the quality goal metrics are represented by quality functions (Q-functions), the P values can be read from the Q-functions generated for the clinical goals, as shown in FIGS. 14A, 14B, for example. The greater the value of the priority P for a goal, the better that goal has been met, and thus the better the quality of the plan for that goal.

From the calculated dose distribution of Step S702, therefore, a set of plan quality values Ps for the current plan can be obtained, one for each of the original clinical goals CG.

Optionally, an overall plan quality for the current plan can also be obtained in Step S703 from the individual current plan qualities by taking the minimum of all the individual goal quality values, for example.

Alternatively, the overall plan quality for the current plan can be obtained by defining an overall plan quality as one that minimizes the difference to the individual plan qualities.

Based on the value P of the overall quality of the current plan in Step S703, a decision can be made as to whether the current plan is acceptable, in which case the current plan becomes the adapted plan. In case the current plan is not acceptable, the control points used as input to the optimization algorithm in S701 are automatically adjusted via multi-resolution adjusting in S705. Adjusting the control points changes the dose distribution in S702, which then changes the plan quality values of the current plan. The total plan quality is then again calculated in S703 to determine whether the subsequently obtained plan is acceptable or whether further adjusting of the control points in S705 is needed.

The multi-resolution adjusting in S705 allows multi-level (four levels for example) adjusting, from a coarse adjustment at level 1, to a fine adjustment at level 4. The level 4 adjustment allows for the fine tuning of the dose distribution.

For each iteration of the optimization algorithm, the decision as to whether the individual plan quality values or the overall plan quality value for the current plan are acceptable can be made by comparing in Step S704 the calculated quality values/value with the plan quality values/ total plan quality value of the original treatment plan, for example. If the differences exceed a predetermined threshold, the result is determined to not be acceptable, in which case the control points (CPs) are gradually modified in S705. The amount of adjustment, and thus the resolution level, can be determined based on the calculated differences.

When accepted, the scheduled plan is optimized to a dose distribution of similar dosimetric characteristics as the dose distribution of the originally planned treatment plan. Thus, the adapted plan should meet the original clinical goals to a similar degree as the original treatment plan.

Figure 15:
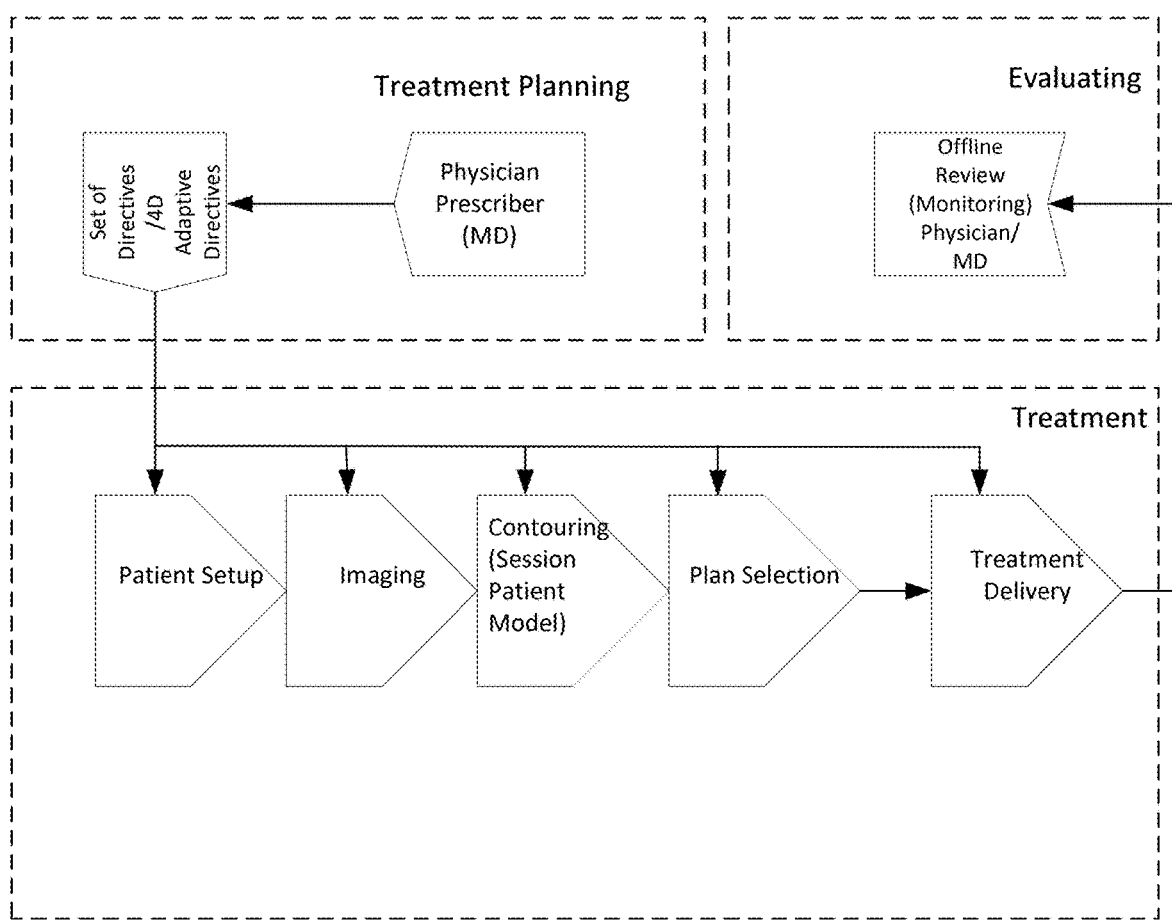
FIG. 15 is an on-couch adaptive workflow, according to various embodiments of the disclosed subject matter.
Figure 16:
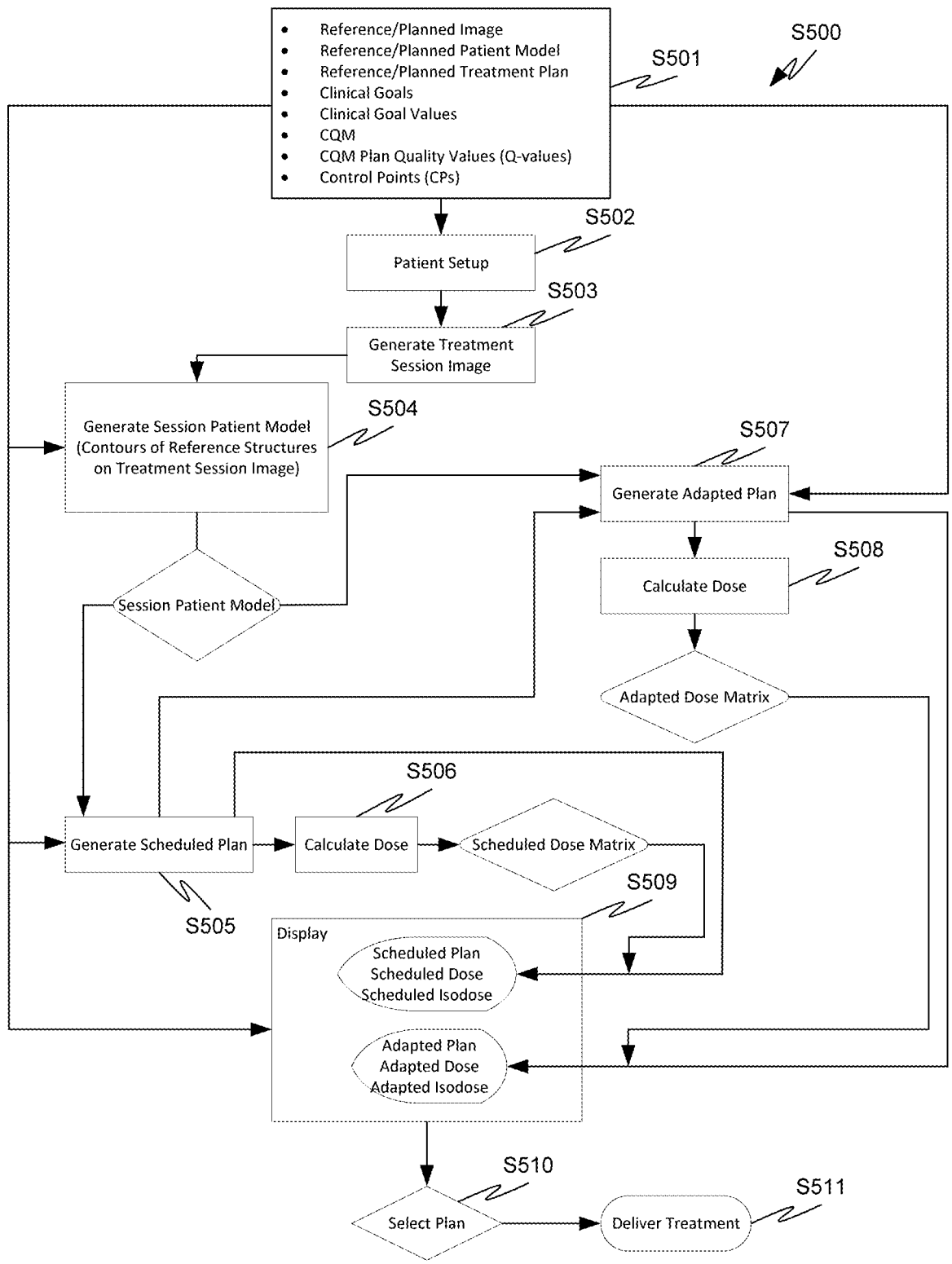
FIG. 16 is a process flow diagram for a session patient model, a scheduled plan and an adapted plan generation, according to various embodiments of the disclosed subject matter.
Figure 17:
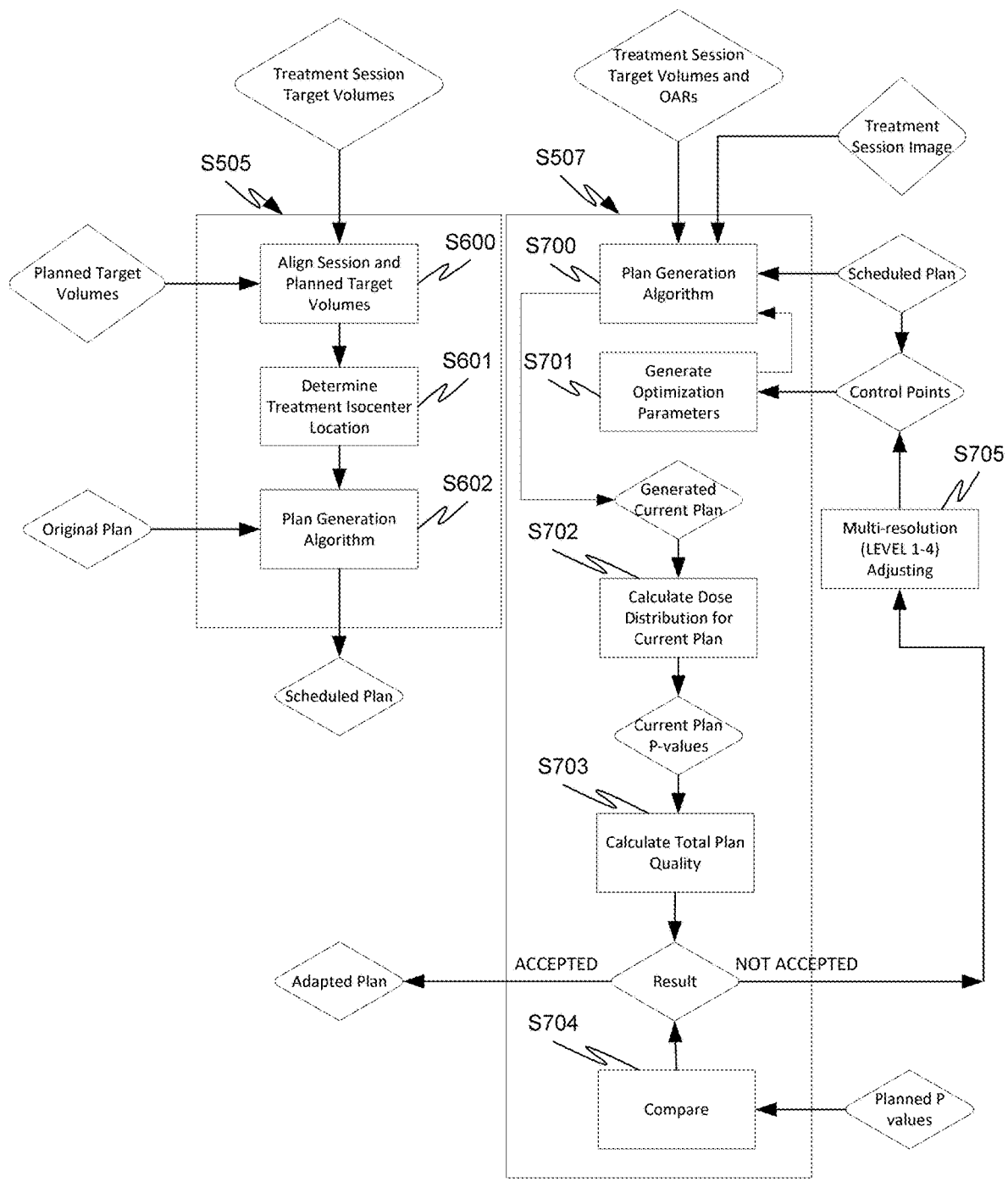
FIG. 17 is a process flow diagram for a an automatic generation and optimization of an adapted plan, according to various embodiments of the disclosed subject matter.

The adapted plan generated in S507 can also be applied to a dose calculation algorithm to calculate the radiation dose in S508 be applied to the session target volume according to the adapted plan. The adapted dose matrix so generated can be sent together with the generated adapted plan and adapted isodose values to the display device to be displayed for the user in S509, for the user to select in S510 the appropriate plan to be delivered in S511 to the patient. Once the user selects a treatment plan, the radiation treatment will proceed in S511 according to the selected plan. The prescribing physician which generated the original treatment plan, the adaptive directives, and the adaptive workflow, or any other qualified physician, can review and/or monitor the treatment delivery offline, as shown in FIG. 15.

It is thus apparent that the disclosed subject matter enables an automated workflow for an adaptive radiation therapy session, to obtain a set of directives, the set of directives including plan quality values of an original treatment plan for a patient; generate a session patient model using information from the set of directives; and generate an adapted treatment plan for the session patient model based on a previous treatment plan optimized based on the plan quality values of the original treatment plan.

It is also apparent that the disclosed subject matter enables the automated generation of an adapted plan based on information from a previous treatment plan, where the amount of information used for generating the adapted plan depends on the quality of the previous plan.

It is also apparent that the disclosed subject matter allows for the automatic generation and optimization of treatment plans based on different input metrics.

It is also apparent that the disclosed subject matter allows for the automatic modification of clinical goals if the goals are conflicting.

It is also apparent that the disclosed subject matter allows for the automatic selection of helper objectives.

It is also apparent that an automatic treatment planning system is disclosed, comprising: a user interface; and a treatment planning module configured to automatically generate one or more treatment plan candidates based on a weighted combination of a first set of objectives derived for clinical data of a first data source and a second set of objectives derived for clinical data of a second, different data source received via the user interface.

The first data source may include a prioritized set of clinical goals, and the second data source may include knowledge-based information.

The treatment planning module may comprise: a function generator configured to generate a cost function for the combined set of objectives; and an ptimizer configured to generate the one or more treatment plan candidates based on the generated cost function.

The treatment planning module may further be configured to: generate a first cost function representing the first set of objectives; and generate a second cost function representing the second set of objectives; wherein the cost function is a weighted combination of the first cost function and the second cost function.

The first cost function may be obtained via a goal-based approach, and the second cost function may be obtained via a knowledge-based approach.

The optimizer may further be configured to determine treatment parameters for the treatment plan candidates, wherein the treatment parameters may be executable by a processing unit of a treatment device to operate the treatment device according to the selected treatment plan candidate.

The first treatment plan candidate may include a weighting factor (m) of 10% for the second cost function, and a second treatment plan candidate may include a weighting factor (m) of 90% for the second cost function.

The system may further comprise a selector configured to allow for the selection by a user of a treatment plan candidate from the generated treatment plan candidates.

A method for automatically generating a plurality of treatment plan candidates is also disclosed, that may comprise: receiving, via a user interface, a first set of clinical data from a first data source, and a second set of clinical data from a second data source; generating a first cost function for the first set of clinical data; generating a second cost function for the second set of clinical data; generating a cost function for the combined first and second set of clinical data, wherein the cost function is a weighted sum of the first cost function and the second cost function; and generating a plurality of treatment plan candidates by optimizing the cost function, wherein the optimization is influenced by a weighting value of the second cost function.

The first source of clinical data may include a prioritized set of clinical goals, and a second source of clinical data may include knowledge-based information.

The first cost function may be obtained using a clinical goal-based approach, and the second cost function may be obtained using a knowledge-based approach.

The method may further comprise: selecting a treatment plan candidate from the plurality of treatment plan candidates; and determining treatment parameters for the selected treatment plan candidate, the treatment parameters being executable by a processing unit of a treatment device to operate the treatment device according to the selected treatment plan candidate.

An automatic treatment planning system is also disclosed that may comprise: a user interface; and a treatment planning module configured to automatically generate a treatment plan candidate based on a prioritized set of clinical goals obtained via the user interface and a set of clinical goals converted from Dose Volume Histogram (DVH) estimates obtained using a knowledge-based DVH model.

The treatment planning module may be configured to: obtain, for each relevant structure of a patient, a Dose Volume Histogram (DVH) estimate based on the DVH model; convert the DVH estimate into a clinical goal; generate a quality metric based on the prioritized set of clinical goals and the clinical goals converted from the DVH estimates; generate a cost function based on the quality metric; and generate a treatment plan based on the cost function.

The converting of the DVH estimate into a clinical goal may include: comparing a DVH line representing a current DVH for a structure with a DVH line representing the DVH estimate; and calculating a value representing differences between the current and the estimate DVH lines.

The calculating of the value may include calculating a sum of the square of negative differences between the current and estimate DVH lines.

The negative differences may represent differences between the current and estimate DVH lines over the entire DVH line.

The generated clinical goals may include corresponding priorities.

The treatment planning module may further comprise: a quality metric generator to generate the quality metric, wherein relative priorities of both the prioritized clinical goals and the converted clinical goals are configured to be dynamically modified by a user via the user interface.

The automatic treatment planning system may further comprise: an optimizer to generate treatment plan parameters by optimizing the cost function; and a controller to control the optimization based on the quality metric.

A method for generating a treatment plan is also disclosed that may comprise: applying a knowledge-based model to generate estimate DVH lines for structures of a patient; converting the estimate DVH lines into a set of generated clinical goals, each generated clinical goal including a priority; generating a quality metric based on the generated clinical goals and prioritized clinical goals obtained from a first source of clinical data via a user interface; generating a cost function based on the quality metric; and generating a treatment plan by optimizing the cost function, wherein relative priorities of the prioritized clinical goals and relative priorities of the generated clinical goals are configured to be dynamically modified by a user via the user interface, and wherein the optimizing is guided by the quality metric.

The converting may include: comparing a DVH line representing a current DVH for a structure with a DVH line representing the DVH estimate; and calculating a value representing differences between the current and estimate DVH lines.

The calculating of the value may include calculating a sum of the square of negative differences between the current and estimate DVH lines, wherein the negative differences represent differences between the current and estimate DVH lines over the entire DVH line.

The method for generating a treatment plan may further comprise generating treatment plan parameters based on the optimized cost function, the treatment plan parameters being configured to be executed by a treatment device.

An automatic treatment planning system is also disclosed that may comprise: a user interface; and a treatment planning module configured to automatically generate a treatment plan based on objectives derived for clinical goals received via the user interface, wherein the objectives include dose objectives and helper objectives.

The helper objectives may be automatically generated.

A helper objective may be generated for each of the clinical goals that are missing adequate dose information.

The treatment planning module may comprise: a quality metric generator generating quality metrics based on the clinical goals; a dose objective generator configured to automatically generate a helper objective for each of the quality metrics, each helper objective shaping a dose objective of a respective quality metric; a cost function generator configured to generate a cost function representing the objectives; and an optimizer configured to generate the treatment plan based on the cost function.

The treatment planning module may further be configured to evaluate the generated helper objectives for conflict with respective dose objectives.

The optimizer may be configured to optimize the cost function and determine plan parameters for the treatment plan.

A method for automatically selecting helper objectives for a given input of clinical goals is also disclosed that may comprise: generating dose objectives for the clinical goals; and when the dose objectives do not achieve a desired dose coverage, automatically generate helper objectives to shape the dose objectives of respective clinical goals, wherein the generating of the helper objectives includes offsetting dose or volume positions of DVH curves generated for the clinical goals.

The input clinical goals may be prioritized clinical goals.

A system for automatically modifying user defined prioritized clinical goals during a conflict in treatment planning is also disclosed that may comprise: an optimizer configured to automatically generate fluences that satisfy user defined prioritized clinical goals in order of their priority; wherein when there is a conflict between two clinical goals, the optimizer is configured to automatically modify the lower priority clinical goal until all higher priority goals are attained and the conflict is resolved.

The system may further comprise a storage medium to store the modified set of prioritized clinical goals as a best clinical goal optimizer (CGO) state.

The system may further comprise a plan quality function generator configured to generate one or more plan quality functions based on quality metrics generated using the adapted set of prioritized clinical goals.

The system may further comprise a treatment planning module configured to generate a treatment plan based on the generated one or more plan quality functions.

An automated workflow for an adaptive radiation therapy session is also disclosed that may comprise: obtaining a set of directives, the set of directives including plan quality values of an original treatment plan for a patient; generating a session patient model using information from the set of directives; and generating an adapted treatment plan for the session patient model, wherein the adapted treatment plan is generated by: using a scheduled treatment plan as input to a treatment plan generation algorithm to generate a current plan, wherein the plan generation algorithm includes optimization parameters which are automatically generated based on control points of the scheduled treatment plan; and generating the adapted treatment plan by optimizing the current plan based on the plan quality values of the original treatment plan.

The workflow may further comprise: determining dose distribution for the current plan based on the control points of the scheduled treatment plan; determining a plan quality value for the current plan based on the determined dose distribution; and comparing the determined plan quality value to an original plan quality value, wherein the control points used for optimizing the current plan are incrementally adjusted based on the result of the comparison.

The set of directives may include information regarding planned radiation dose, planned clinical goals, planned clinical goal values, reference patient model, reference treatment plan, and one or more reference images.

The scheduled treatment plan for the session patient model can be a previously generated plan.

Systems including a computer processing device configured to execute a sequence of programmed instructions embodied on a computer-readable storage medium, the execution thereof causing the system to execute any or alternatively a combination of any of the method steps disclosed herein, are also disclosed.

A non-transitory computer-readable storage medium upon which is embodied a sequence of programmed instructions for the generation of day to day treatment images to be used in adaptive radiation therapy, and a computer processing system that executes the sequence of programmed instructions embodied on the computer-readable storage medium are also disclosed. Execution of the sequence of programmed instructions can cause the computer processing system to execute the automatic treatment planning and optimization processes described herein.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The terms "system," "device," and "module" have been used interchangeably herein, and the use of one term in the description of an embodiment does not preclude the application of the other terms to that embodiment or any other embodiment.

Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. An automatic treatment planning system, comprising:
a user interface; and
a processing device configured to:
    receive, via the user interface, clinical data of a first data source and clinical data of a second data source, the second data source being of a different type than the first data source; and
    execute a sequence of programmed instructions embodied on a computer-readable storage medium to generate one or more treatment plan candidates based on the received clinical data;
the processing device comprising a treatment planning module configured to:
    derive a first set of objectives for the clinical data of the first data source;
    derive a second set of objectives for the clinical data of the second data source;
    combine the first set of objectives and the second set of objectives using a weighting factor; and
    automatically generate one or more treatment plan candidates based on the weighted combination of the first set of objectives and the second set of objectives;
the processing device being further configured to send the treatment plan candidates to a controller of a treatment device to operate the treatment device according to a selected treatment plan candidate.

2. The system of claim 1, wherein the first data source includes a prioritized set of clinical goals, and the second data source includes knowledge-based information.

3. The system of claim 2, wherein the treatment planning module comprises:
a function generator configured to generate a cost function ($C_{Total}$) for the combined set of objectives; and
an optimizer configured to generate the one or more treatment plan candidates based on the generated cost function.

4. The system of claim 3, wherein the treatment planning module is further configured to:
generate a first cost function ($C_G$) representing the first set of objectives; and
generate a second cost function ($C_K$) representing the second set of objectives;
wherein the cost function ($C_{Total}$) is a weighted combination of the first cost function and the second cost function ($C_{Total}=C_G+mC_K$).

5. The system of claim 4, wherein the first cost function ($C_G$) is obtained via a goal-based approach, and the second cost function ($C_K$) is obtained via a knowledge-based approach.

6. The system of claim 5, wherein the optimizer is further configured to determine treatment parameters for the treatment plan candidates, wherein the treatment parameters are executable by a processing unit of a treatment device to operate the treatment device according to the selected treatment plan candidate.

7. The system of claim 6, wherein a first treatment plan candidate includes a weighting factor (m) of 10% for the second cost function, and a second treatment plan candidate includes a weighting factor (m) of 90% for the second cost function.

8. The system of claim 1, further comprising a selector configured to allow for the selection by a user of a treatment plan candidate from the generated treatment plan candidates.

9. A method for automatically generating a plurality of treatment plan candidates, comprising:
executing a sequence of programmed instructions embodied on a computer-readable storage medium of a processing device to:
    receive, via a user interface of the processing device, a first set of clinical data from a first data source, and a second set of clinical data from a second data source, the second data source being of different type than the first data source;
    generate a first cost function for the first set of clinical data;
    generate a second cost function for the second set of clinical data;
    generate a cost function for the combined first and second set of clinical data, wherein the cost function is a weighted sum of the first cost function and the second cost function; and
    generate a plurality of treatment plan candidates by optimizing the cost function, wherein the optimization is influenced by a weighting value of the second cost function,
the treatment plan candidates being configured to be supplied by the processing device to a controller of a treatment device to operate the treatment device according to a selected treatment plan candidate.

10. The method of claim 9, wherein the first source of clinical data includes a prioritized set of clinical goals, and a second source of clinical data includes knowledge-based information.

11. The method of claim 10, wherein the first cost function is obtained using a clinical goal-based approach, and the second cost function is obtained using a knowledge-based approach.

12. The method of claim 11, wherein a first treatment plan candidate is obtained for a weighting value of 10% for the second cost function, and a second treatment plan is obtained for weighting value of 90% for the second cost function.

13. The method of claim 9, further comprising:
selecting a treatment plan candidate from the plurality of treatment plan candidates; and
determining treatment parameters for the selected treatment plan candidate, the treatment parameters being executable by a processing unit of a treatment device to operate the treatment device according to the selected treatment plan candidate.

* * * * *